United States Patent

Kriesel et al.

[11] Patent Number: 5,906,592
[45] Date of Patent: *May 25, 1999

[54] FLUID DELIVERY APPARATUS

[75] Inventors: Marshall S. Kriesel, St. Paul; Farhad Kazemzadeh, Bloomington; Matthew B. Kriesel, St. Paul, all of Minn.; William W. Feng, Lafayette, Calif.; Steve C Barber, Shorewood, Minn.; William J. Kluck, Hudson, Wis.

[73] Assignee: Science Incorporated, Bloomington, Minn.

[ * ] Notice: This patent is subject to a terminal disclaimer.

[21] Appl. No.: 08/907,564

[22] Filed: Aug. 8, 1997

Related U.S. Application Data

[63] Continuation of application No. 08/451,520, May 26, 1995, Pat. No. 5,656,032, which is a continuation-in-part of application No. 08/129,693, Sep. 29, 1993, Pat. No. 5,419,771, which is a continuation-in-part of application No. 08/069,937, May 28, 1993, Pat. No. 5,336,188, which is a continuation-in-part of application No. 08/046,438, May 18, 1993, Pat. No. 5,411,480, which is a continuation-in-part of application No. 07/987,021, Dec. 7, 1992, Pat. No. 5,279,558, which is a continuation-in-part of application No. 07/870,269, Apr. 17, 1992, Pat. No. 5,205,820, which is a continuation-in-part of application No. 07/642,208, Jan. 16, 1991, Pat. No. 5,169,389, which is a continuation-in-part of application No. 07/367,304, Jun. 16, 1989, Pat. No. 5,019,047.

[51] Int. Cl.$^6$ .................................................. A61M 37/00
[52] U.S. Cl. ....................... 604/132; 604/246; 604/890.1; 128/DIG. 12
[58] Field of Search ................................ 604/48, 93, 131, 604/132, 151, 153, 890.1, 246; 128/DIG. 12

[56] References Cited

U.S. PATENT DOCUMENTS

| | | | |
|---|---|---|---|
| 4,193,397 | 3/1980 | Tucker et al. | 604/83 |
| 4,668,231 | 5/1987 | DeVries et al. | 604/891 |
| 4,968,301 | 11/1990 | Di Palma et al. | 604/132 |
| 4,969,873 | 11/1990 | Steinbach et al. | 604/93 |
| 5,176,641 | 1/1993 | Idriss | 604/133 |
| 5,205,820 | 4/1993 | Kriesel | 604/85 |
| 5,298,025 | 3/1994 | Hessel et al. | 604/93 |

*Primary Examiner*—Corrine McDermott
*Attorney, Agent, or Firm*—James E. Brunton

[57] ABSTRACT

An apparatus for accurately infusing fluids into a patient at specific rates over an extended period of time and the method for making same. The apparatus includes one or more dispensers of a low profile, laminate or layered construction each having a stored energy source in the form of a distendable membrane or an elastomeric cellular mass, which in cooperation with the base, defined a fluid chamber having a fluid inlet and a fluid outlet. The apparatus further includes, in lieu of a rigid ullage, a high novel, conformable ullage made of yieldable materials. The conformable ullage uniquely conforms to the shape of elastomeric membrane as the membrane returns to its less distended configuration. This arrangement will satisfy even the most stringent delivery tolerance requirements and will elegantly overcome the limitations of materials selection encountered in devices embodying the rigid ullage construction. Additionally, with the novel ullage construction, the ullage can be located either between the base and the fluid to be delivered, or alternatively, can be located between the elastomeric membrane and the fluid to be delivered. Further, a plurality of subreservoirs can be associated with a single ullage thereby making it possible to incorporate a wide variety of delivery profiles within a single device.

36 Claims, 14 Drawing Sheets

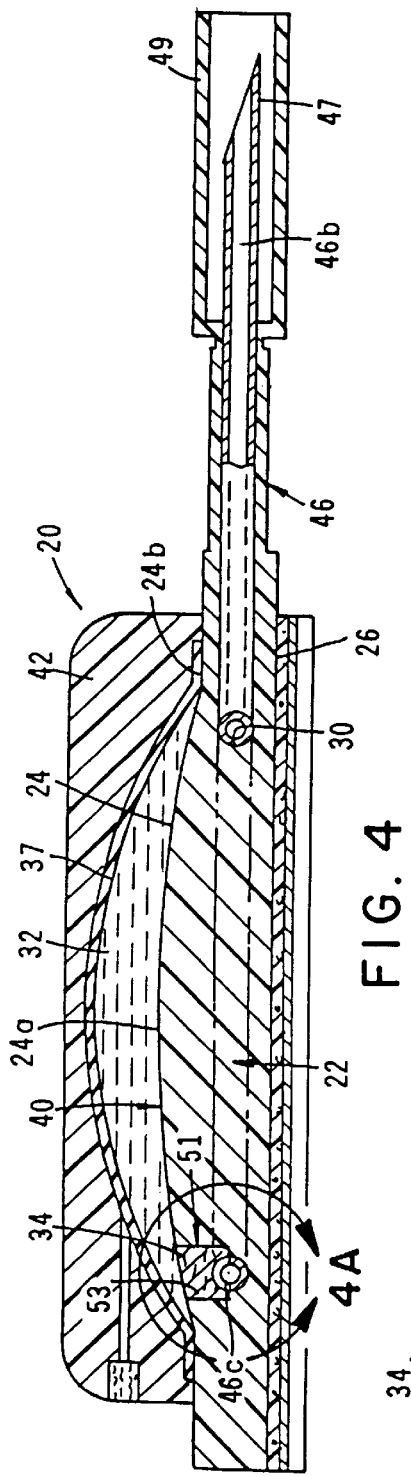
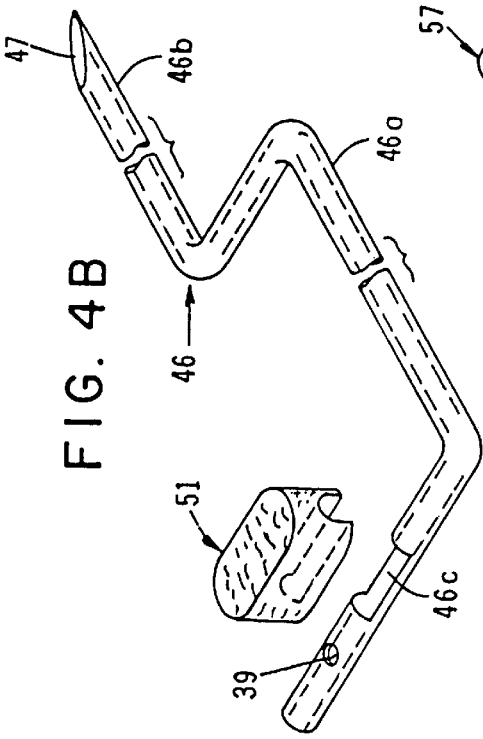
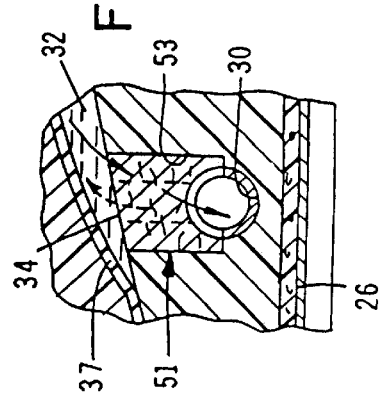
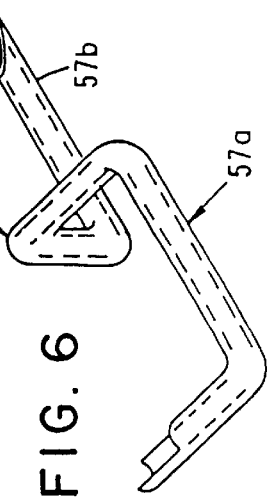
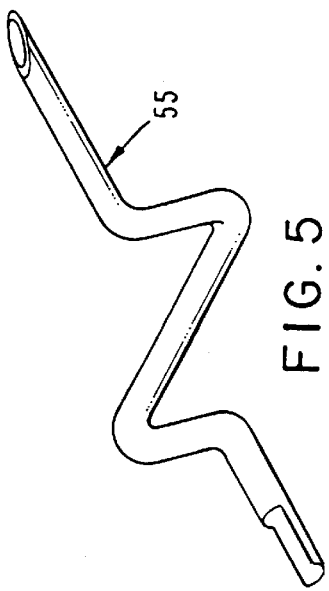
FIG. 4
FIG. 4A
FIG. 4B
FIG. 5
FIG. 6

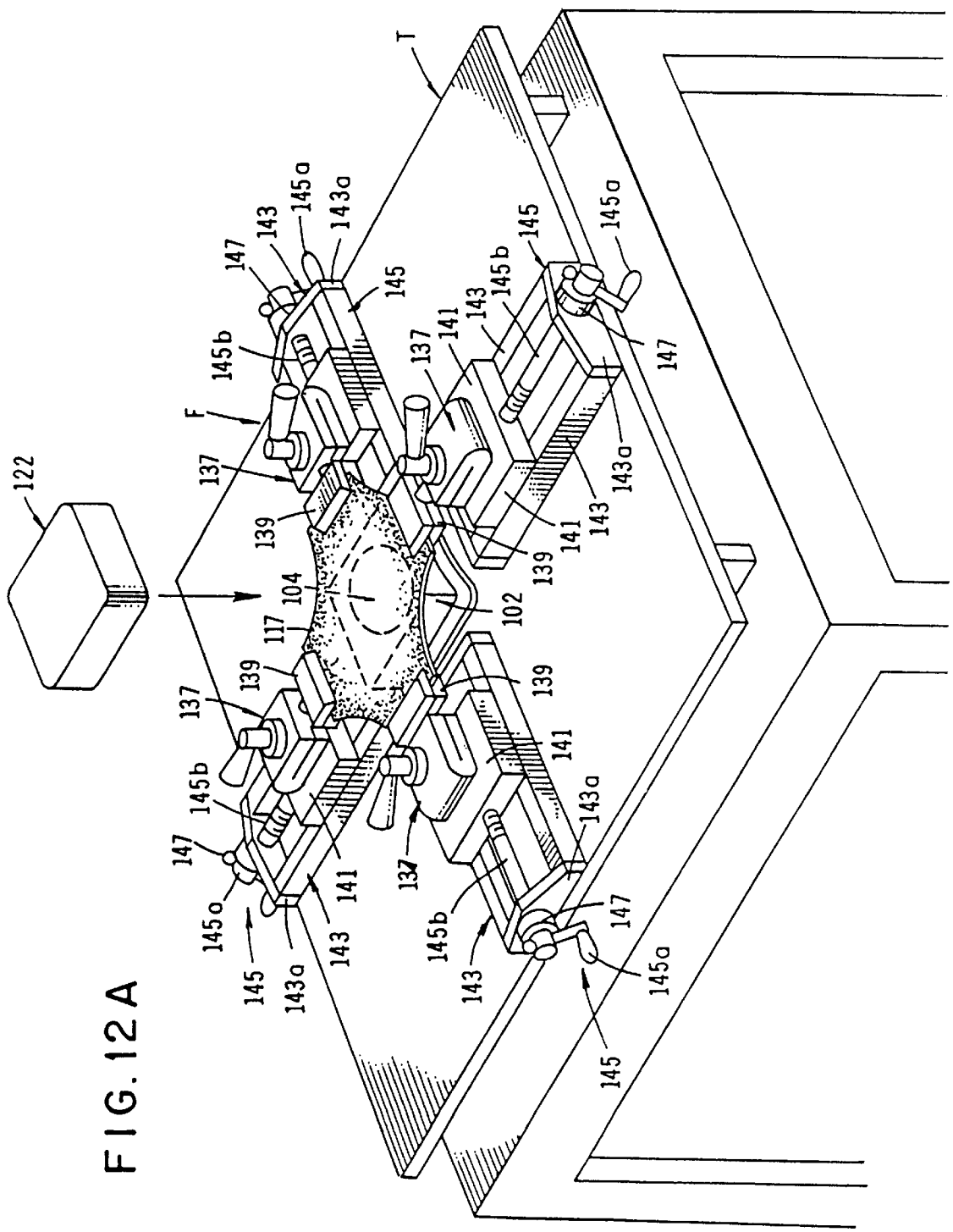

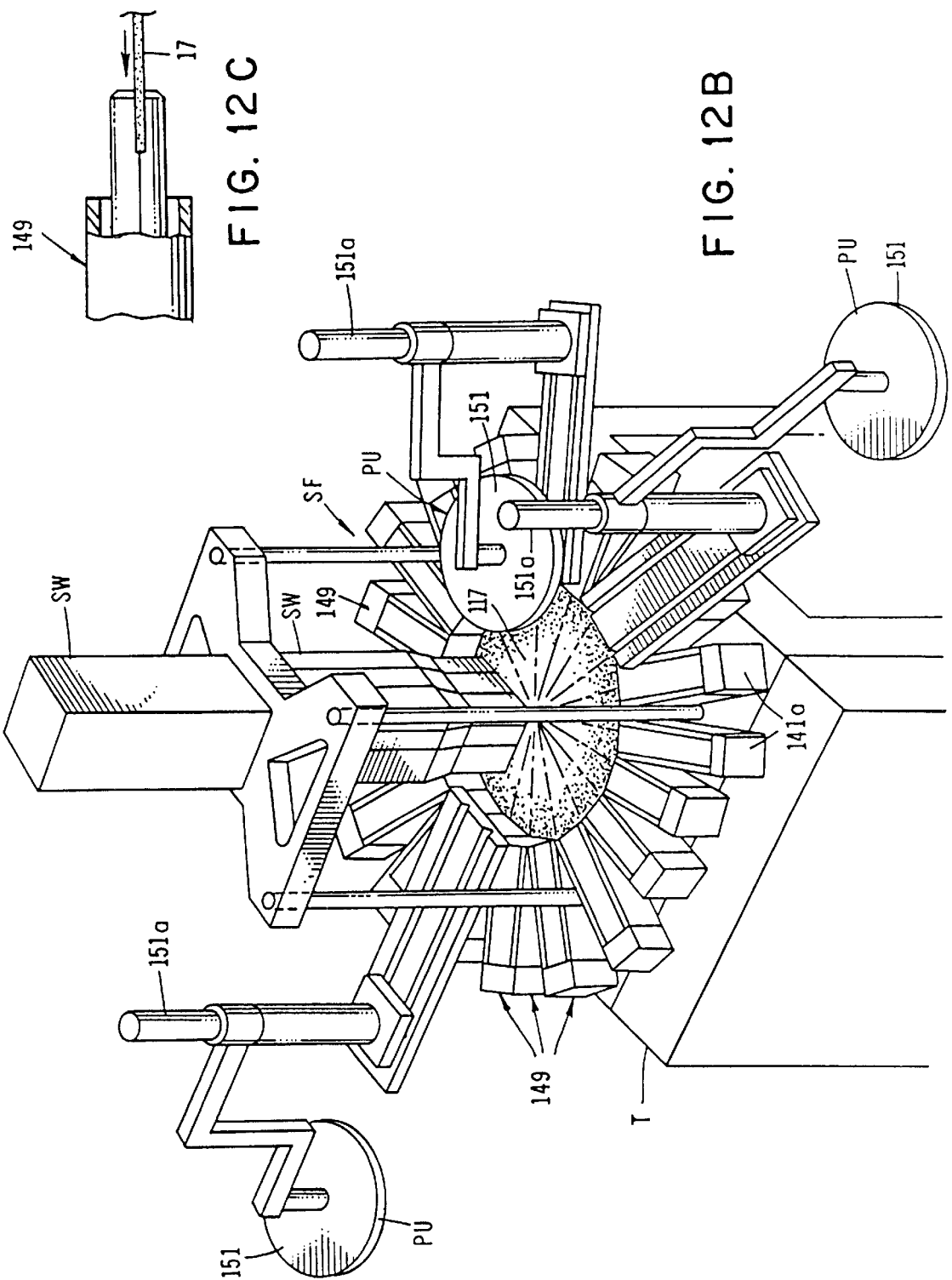

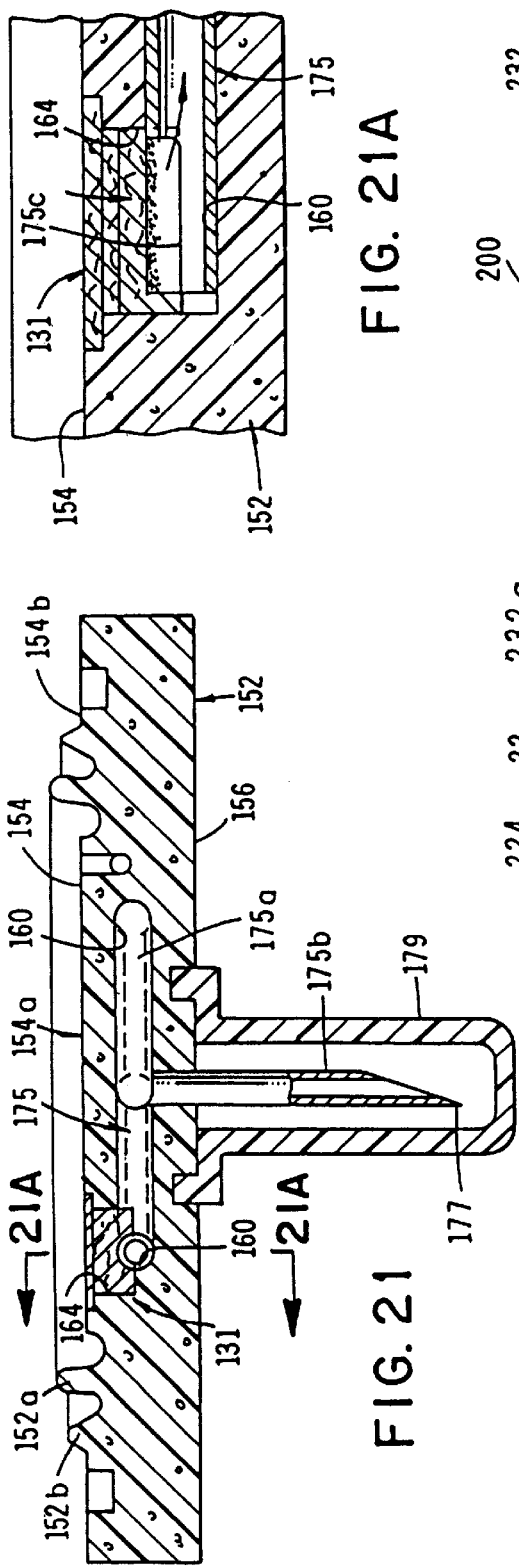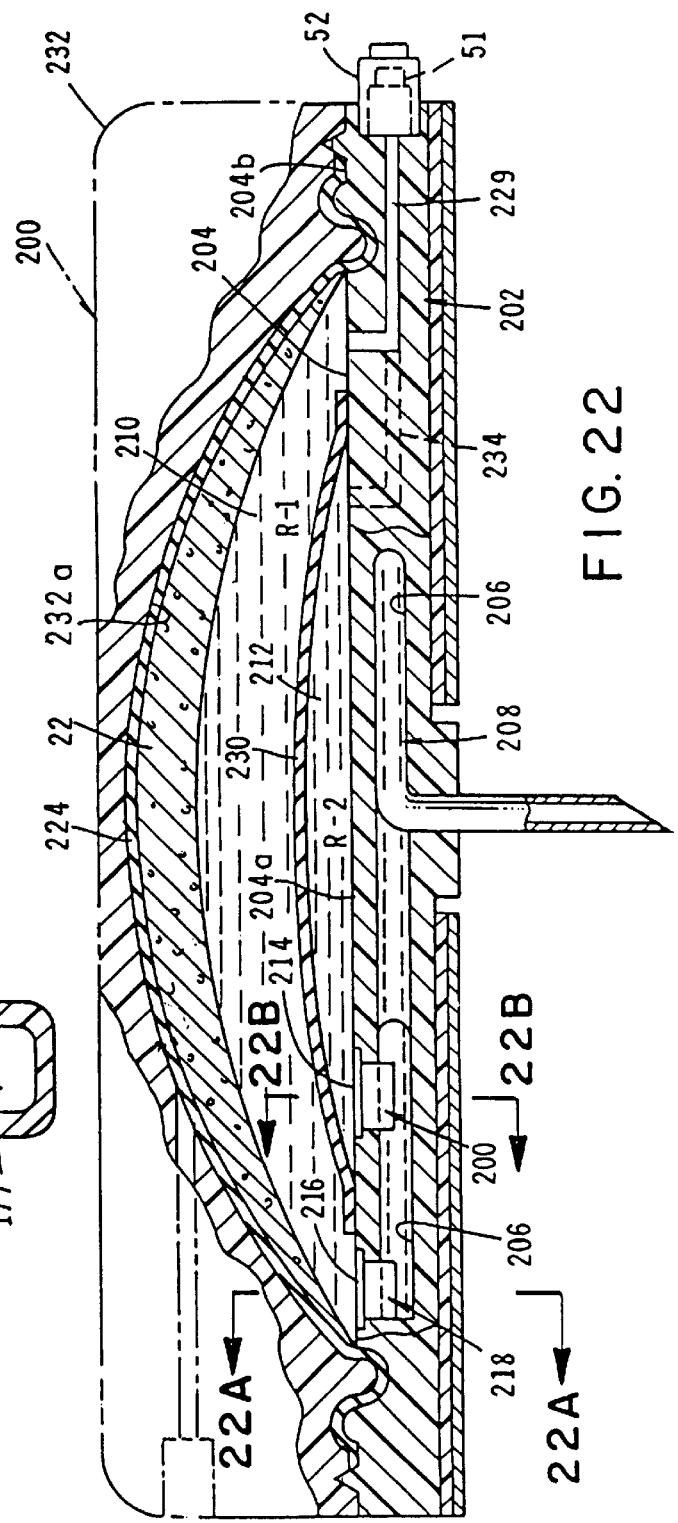

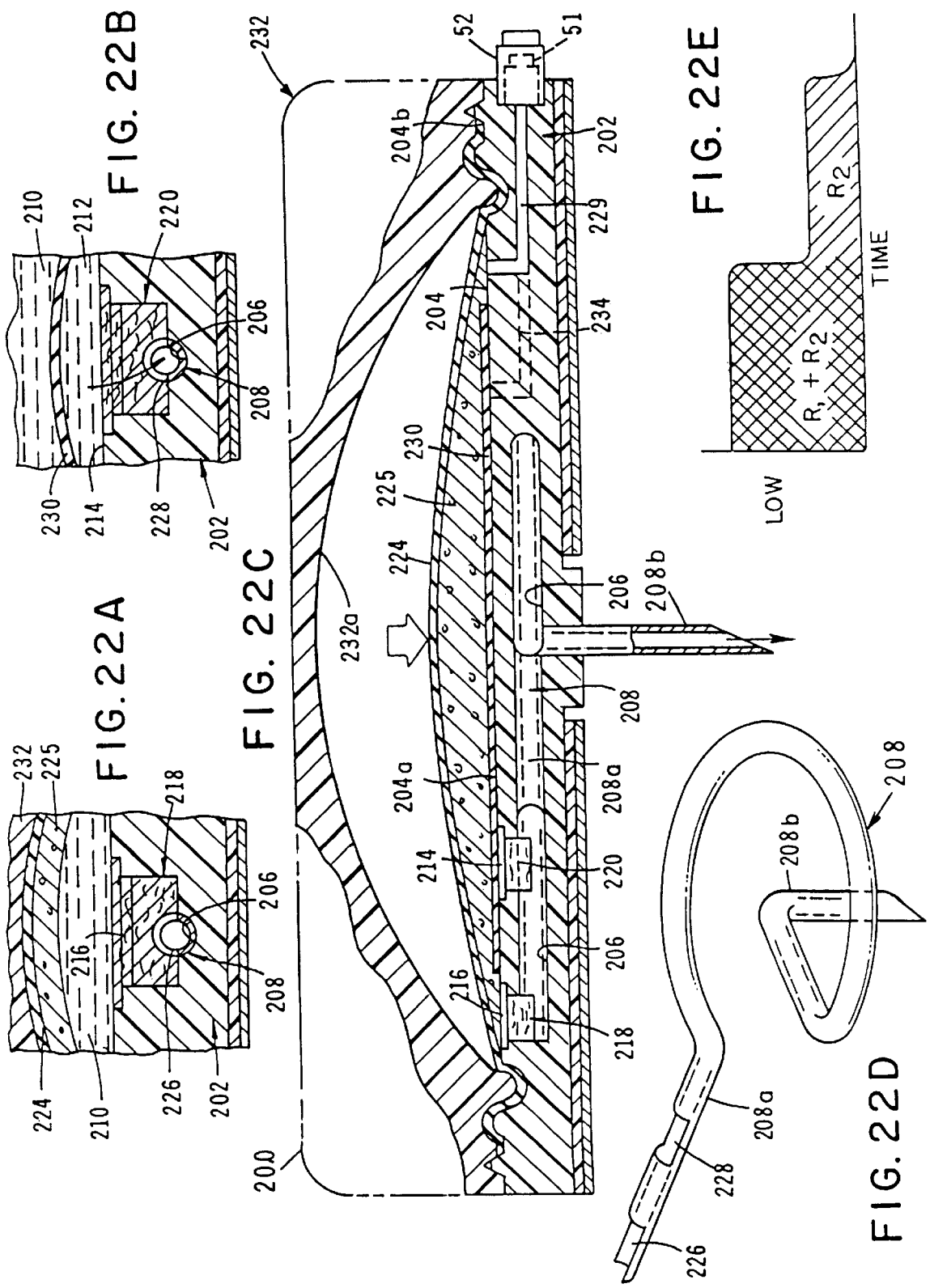

FLUID DELIVERY APPARATUS

This is a Continuation of application Ser. No. 08/451,520, filed May 26, 1995 now U.S. Pat. No. 5,656,032; which is a Continuation In Part application of application Ser. No. 08/129,693, filed Sep. 29, 1993 now U.S. Pat. No. 5,419,771; which is a Continuation In Part application of application Ser. No. 08/069,937, filed May 28, 1993 which has now issued into U.S. Pat. No. 5,336,188; which is a Continuation In Part of application, Ser. No. 08/046,438 filed May 18, 1993 which has now issued into U.S. Pat. No. 5,411,480; which is a Continuation In Part of application Ser. No. 07/987,021 filed Dec. 7, 1992 which has now issued into U.S. Pat. No. 5,279,558; which is a Continuation In Part application of application Ser. No. 07/870,269 filed Apr. 17, 1992 which has now issued into U.S. Pat. No. 5,205,820; which is a Continuation In Part of application Ser. No. 07/642,208 filed Jan. 16, 1991, which has now issued to U.S. Pat. No. 5,169,389 which is a Continuation In Part of application Ser. No. 07/367,304 filed Jun. 16, 1989 which has now issued to U.S. Pat. No. 5,019,047.

BACKGROUND OF THE INVENTION

1. Field of the Invention

The present invention relates generally to fluid delivery devices. More particularly, the invention concerns an improved apparatus for infusing medicinal agents into an ambulatory patient at specific rates over extended periods of time.

2. Discussion of the Invention

Many medicinal agents require an intravenous route for administration thus bypassing the digestive system and precluding degradation by the catalytic enzymes in the digestive tract and the liver. The use of more potent medications at elevated concentrations has also increased the need for accuracy in controlling the delivery of such drugs. The delivery device, while not an active pharmacologic agent, may enhance the activity of the drug by mediating its therapeutic effectiveness. Certain classes of new pharmacologic agents possess a very narrow range of therapeutic effectiveness, for instance, too small a dose results in no effect, while too great a dose results in toxic reaction.

In the past, prolonged infusion of fluids has generally been accomplished using gravity flow methods, which typically involve the use of intravenous administration sets and the familiar bottle suspended above the patient. Such methods are cumbersome, imprecise and require bed confinement of the patient. Periodic monitoring of the apparatus by the nurse or doctor is required to detect malfunctions of the infusion apparatus.

Devices from which liquid is expelled from a relatively thick-walled bladder by internal stresses within the distended bladder are well-known in the prior art. Such bladder, or "balloon" type, devices are described in U.S. Pat. No. 3,469,578, issued to Bierman and in U.S. Pat. No. 4,318,400, issued to Perry. The devices of the aforementioned patents also disclose the use of fluid flow restrictors external of the bladder for regulating the rate of fluid flow from the bladder.

The prior art bladder type infusion devices are not without drawbacks. Generally, because of the very nature of bladder or "balloon" configuration, the devices are unwieldy and are difficult and expensive to manufacture and use. Further, the devices are somewhat unreliable and their fluid discharge rates are frequently imprecise.

The apparatus of the present invention overcomes many of the drawbacks of the prior art by eliminating the bladder and making use of recently developed elastomeric films, expandable foams and similar materials, which, in cooperation with a base defines a fluid chamber that contains the fluid which is to be dispensed. The elastomeric film membrane or the expandable foam member controllably forces fluid within the chamber into fluid flow channels provided in the base.

The elastomeric film materials used in the apparatus of the present invention, as well as various alternate constructions of the apparatus, are described in detail in U.S. Pat. No. 5,205,820 issued to the present inventor. Therefore, U.S. Pat. No. 5,205,820 is hereby incorporated by reference in its entirety as though fully set forth herein. Co-pending U.S. Ser. No. 08/129,693 filed by the present inventor on Sep. 29, 1993 also describes various types of expandable cellular elastomers and elastomeric foams used in making the expandable member of various physical embodiments of the invention. This co-pending application is also hereby incorporated by reference in its entirety as though fully set forth herein.

The apparatus of the present invention can be used with minimal professional assistance in an alternate health care environment, such as the home. By way of example, devices of the invention can be comfortably and conveniently removably affixed to the patient's body and can be used for the continuous infusion of antibiotics, hormones, steroids, blood clotting agents, analgesics, and like medicinal agents. Similarly, the devices can be used for I-V chemotherapy and can accurately deliver fluids to the patient in precisely the correct quantities and at extended microfusion rates over time.

One of the embodiments of the invention described in Continuation-In-Part application Ser. No. 08/129,693 comprises a generally circular base assembly and a stored energy means provided in the form of a thin, generally circular shaped, pre-stressed distendable elastomeric membrane which cooperates with the base assembly to form a fluid reservoir. Superimposed over the base assembly is a rigid, distendable membrane engagement means which provides an ullage within the reservoir.

The embodiments of the invention described herein comprise improvements to the devices described in U.S. Pat. No. 5,205,820 and in U.S. Ser. No. 08/129,693. More particularly, the inventions described herein are directed toward providing novel fluid delivery devices which are extremely low profile and are eminently capable of meeting the most stringent of fluid delivery tolerance requirements. In this regard, medical and pharmacological research continues to reveal the importance of the manner in which a medicinal agent is administered. The delivery device, while not an active pharmacological agent, may enhance the activity of the drug by mediating its therapeutic effectiveness. For example, certain classes of pharmacological agents possess a very narrow dosage range of therapeutic effectiveness, in which case too small a dose will have no effect, while too great a dose can result in toxic reaction. In other instances, some forms of medication require an extended delivery time to achieve the utmost effectiveness of a medicinal therapeutic regimen.

By way of example, the therapeutic regimens used by insulin-dependent diabetics provide a good example of the benefits of carefully selected delivery means. The therapeutic object for diabetics is to consistently maintain blood glucose levels within a normal range. Conventional therapy involves injecting insulin by syringe several times a day, often coinciding with meals. The dose must be calculated based on glucose levels present in the blood. If the dosage is off, the bolus administered may lead to acute levels of either glucose or insulin resulting in complications, including unconsciousness or coma. Over time, high concentrations of glucose in the blood can also lead to a variety of chronic health problems, such as vision loss, kidney failure, heart disease, nerve damage, and amputations.

A recently completed study sponsored by the National Institutes of Health (NIH) investigated the effects of different therapeutic regimens on the health outcomes of insulin dependent diabetics. This study revealed some distinct advantages in the adoption of certain therapeutic regimens. Intensive therapy that involved intensive blood glucose monitoring and more frequent administration of insulin by conventional means, i.e., syringes, throughout the day saw dramatic decreases in the incidence of debilitating complications.

The NIH study also raises the question of practicality and patient adherence to an intensive therapy regimen. A bona fide improvement in insulin therapy management must focus on the facilitation of patient comfort and convenience as well as dosage and administration schemes. Basal rate delivery of insulin by means of a convenient and reliable delivery device over an extended period of time represents one means of improving insulin management. Basal rate delivery involves the delivery of very small volumes of fluid (1–3 mL.) over comparatively long periods of time (18–24 hours). As will be appreciated from the discussion which follows, the apparatus of the present invention is uniquely suited to provide precise fluid delivery management at a low cost in those cases where a variety of precise dosage schemes are of utmost importance.

In those embodiments of the invention described in U.S. Pat. No. 5,205,820 issued to the present inventor and incorporated herein by reference, the fluid delivery apparatus components generally included: a base assembly; an elastomeric membrane serving as a stored energy means; fluid flow channels for filling and delivery; flow control means; a cover; and an ullage, which comprised a part of the base assembly. The ullage in these devices typically comprises a semi-rigid structure having flow channels leading from the top of the structure through the base to inlet or outlet ports of the device.

In the rigid ullage configuration, the stored energy means of the device must be superimposed over the ullage to form the fluid-containing reservoir from which fluids are expelled at a controlled rate by the elastomeric membrane of the stored energy means tending to return to a less distended configuration in a direction toward the ullage. With these constructions, the stored energy membrane is typically used at high extensions over a significantly large portion of the pressure-deformation curve (FIG. 1A).

Elastomeric membrane materials suitable for use as the stored energy means must possess certain physical characteristics in order to meet the performance requirements for a fluid delivery apparatus. More particularly, for good performance, the elastomeric membrane material must have good memory characteristics under conditions of high extension; good resistance to chemical and radiological degradation; and appropriate gas permeation characteristics depending upon the end application to be made of the device.

Once an elastomeric membrane material is chosen that will optimally meet the desired performance requirements, there still remain certain limitations to the level of refinement of the delivery tolerances that can be achieved using the rigid ullage configuration. These result primarily from the inability of the rigid ullage to conform to the shape of the elastomeric membrane near the end of the delivery period. This nonconformity can lead to extended delivery rate tail-off and higher residual problems when extremely accurate delivery is required. For example, when larger volumes of fluid are to be delivered, the tail-off volume represents a smaller portion of the fluid amount delivered and therefore exhibits much less effect on the total fluid delivery profile, but in very small dosages, the tail-off volume becomes a larger portion of the total volume. This sometimes places severe physical limits on the range of delivery profiles that may easily be accommodated using the rigid ullage configuration.

An acceptable elastomeric membrane material candidate for the rigid ullage configuration must also be drug compatible as is typically in contact with any drug containing fluid disposed within the reservoir. Many currently available elastomeric membrane materials, due to their chemical composition or means of manufacturing, are not drug compatible. This compatibility restriction, combined with strict physical requirements, results in further limitation of available selections for the candidate elastomeric material for use in devices embodying a rigid ullage structure.

As will be better appreciated from the discussion which follows, the apparatus of the present invention provides a unique and novel improvement for a disposable dispenser of simple but highly reliable construction that may be adapted to many applications of use. A particularly important aspect of the improved apparatus is the incorporation of a conformable ullage made of yieldable materials, the conformable ullage uniquely conforms to the shape of elastomeric membrane as the membrane returns to its less distended configuration. This novel construction will satisfy even the most stringent delivery tolerance requirements and will elegantly overcome the limitations of materials selection encountered in devices embodying the rigid ullage construction. Another significant advantage of the novel ullage construction is that the ullage can be located either between the base and the fluid to be delivered, or alternatively, can be located between the elastomeric membrane and the fluid to be delivered. Further, a plurality of subreservoirs can be associated with a single ullage thereby making it possible to incorporate a wide variety of delivery profiles within a single device.

Although the infusion devices described in U.S. Pat. No. 5,205,820 and in U.S. Ser. No. 08/129,693 are very low profile devices, the devices of the inventions described herein are designed in a manner so that they can be of even a lower profile thereby making them ideally suited for use in dispensing medicinal agents such as insulin and the like.

SUMMARY OF THE INVENTION

It is an object of the present invention to provide an apparatus having a self-contained stored energy membrane for expelling fluids at a precisely controlled rate which is of a compact, extremely low profile, laminate construction. More particularly, it is an object of the invention to provide such an apparatus which is of very low profile so that it can conveniently be used for the precise infusion of pharmaceutical fluids, such as insulin and the like, into an ambulatory patient at controlled rates over extended periods of time.

It is another object of the invention to provide an apparatus of the aforementioned character which is small, compact, highly reliable and easy-to-use by lay persons in a non-hospital environment.

It is another object of the invention to provide an apparatus as described in the preceding paragraphs which, in one form, can be used for intravenous infusion of fluids and, in a second form, can be used for subdermal infusion of fluids. In this regard, the apparatus includes a novel and unique delivery cannula having a body portion disposed within a circuitous channel formed within the base superstructure of the apparatus and a pierceable portion which extends outwardly from the base of the apparatus. By constructing the cannula in a circuitous configuration, substantial structural stability of the cannula relative to the base is achieved as compared with a straight cannula protruding from the base.

Another object of the invention is to provide an apparatus which embodies a soft, pliable, conformable mass which defines an ullage within the reservoir of the device which will closely conform to the shape of the stored energy membrane thereby effectively avoiding extended flow delivery rate tail-off at the end of the fluid delivery period.

A further object of the invention is to provide a low profile, fluid delivery device of laminate construction which can meet even the most stringent fluid delivery tolerance requirements.

Another object of the invention is to provide an apparatus of the class described which includes a conformable ullage construction that can be used with a plurality of fluid reservoirs of the same or different volume.

Another object of the invention is to provide an apparatus of the character which includes a novel combination filter and rate control assemblage disposed intermediate the fluid reservoir outlet and the outlet port of the device.

Another object of the invention is to provide an apparatus of the character described which, due to its unique construction, can be manufactured inexpensively in large volume by automated machinery.

Other objects of the invention are set forth in U.S. Pat. No. 5,205,820 which is incorporated herein and still further objects will become more apparent from the discussion which follows.

BRIEF DESCRIPTION OF THE DRAWINGS

FIG. 4 is a cross-sectional view taken along lines 4—4 of FIG. 1.

FIG. 4A is an enlarged, fragmentary cross-sectional view of area 4A of FIG. 4.

FIG. 4B is an enlarged, generally perspective view of the cannula and flow control means of the form of the invention shown in FIG. 1.

FIG. 5 is an enlarged, generally perspective view of an alternate form of infusion cannula of the invention.

FIG. 6 is an enlarged, generally perspective view of still another alternate form of infusion cannula.

FIG. 12A is a generally perspective view illustrating the membrane biaxial stretching step of the method of the invention.

FIG. 12B is a generally perspective view illustrating an alternate method of radially stretching the distendable membrane.

FIG. 12C is a fragmentary, cross-sectional view illustrating the construction of the hydraulically actuated gripping fingers that grip the membrane.

FIG. 21 is a cross-sectional view of the base portion of the embodiment of the invention shown in FIG. 20.

FIG. 21A is a cross-sectional view taken along lines 21A—21A of FIG. 21.

FIG. 22 is a cross-sectional view of still another embodiment of the invention showing an infusion device embodying a conformable ullage and a plurality of subreservoirs.

FIG. 22A is a cross-sectional view taken along lines 22A—22A of FIG. 22.

FIG. 22B is a cross-sectional view taken along lines 22B—22B of FIG. 22.

FIG. 22C is a cross-sectional view similar to FIG. 22, but showing the configuration of the device after the fluid has been dispensed therefrom.

FIG. 22D is a generally perspective view of the infusion cannula of the device shown in FIG. 22.

FIG. 22E is a generally graphical representation depicting the character of the fluid flow from the dual reservoir apparatus shown in FIG. 22.

DESCRIPTION OF THE INVENTION

Figure 1:
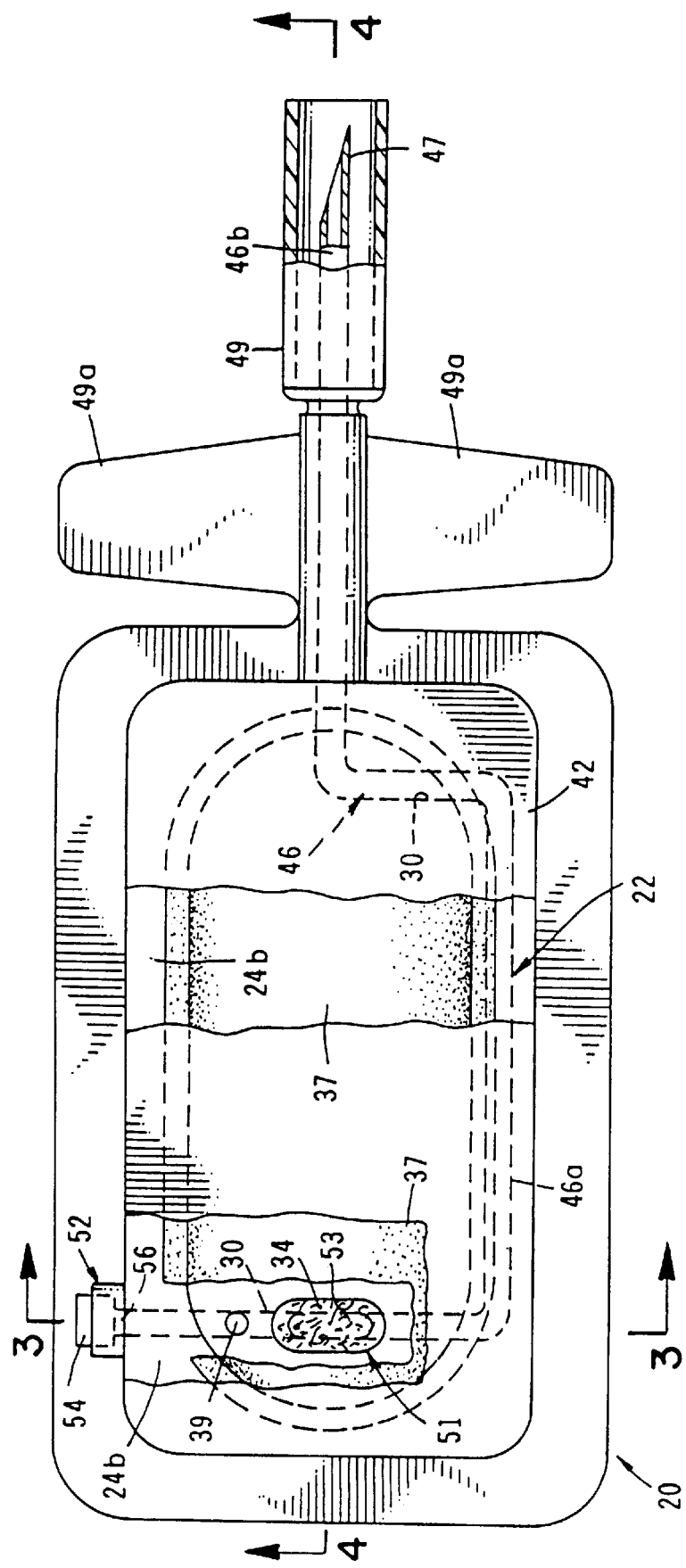
FIG. 1 is a top plan view of one form of an ultra low profile device of the invention partly broken away to show internal construction.

Referring to the drawings and particularly to FIGS. 1 through 4, one form of the ultra low profile device of the invention for use in intravenous infusion of medicinal fluid into a patient is there shown and generally designated by the numeral 20. As best seen by referring to FIGS. 3 and 4, the embodiment of the invention there shown comprises a thin base 22 having an upper surface 24 including a central portion 24a and peripheral portion 24b circumscribing central portion 24a. Base 22 is provided with a lower surface 26 which is engagable with the patient when the device is taped or otherwise removably affixed to the patient. Formed within base 22 is a circuitous channel 30 (FIGS. 1 and 2), the purpose of which will presently be described.

Figure 2:
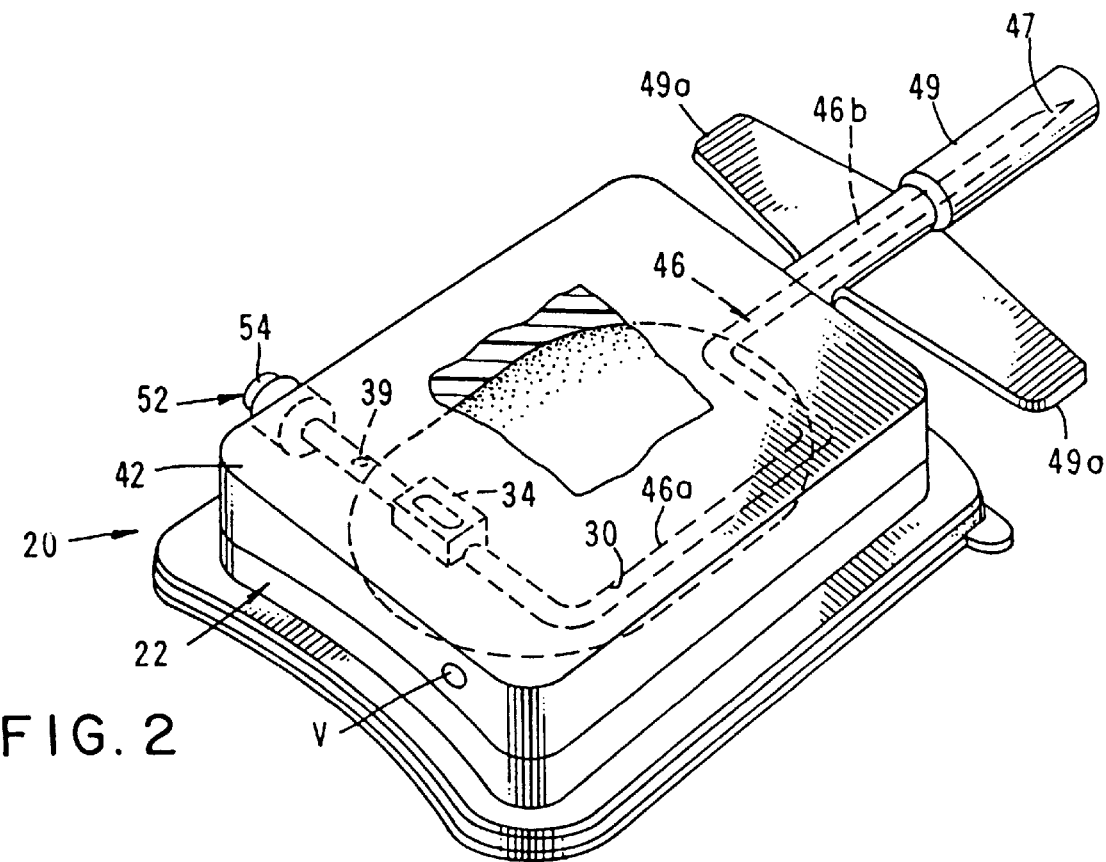
FIG. 2 is a generally perspective view of the ultra low profile infusion device shown in FIG. 1.
Figure 3:
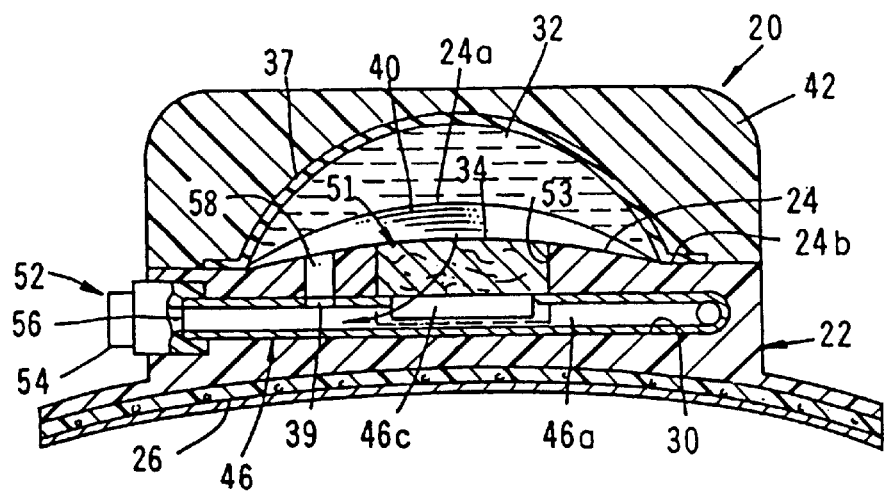
FIG. 3 is a cross-sectional view taken along lines 3—3 of FIG. 1.
Figure 7:
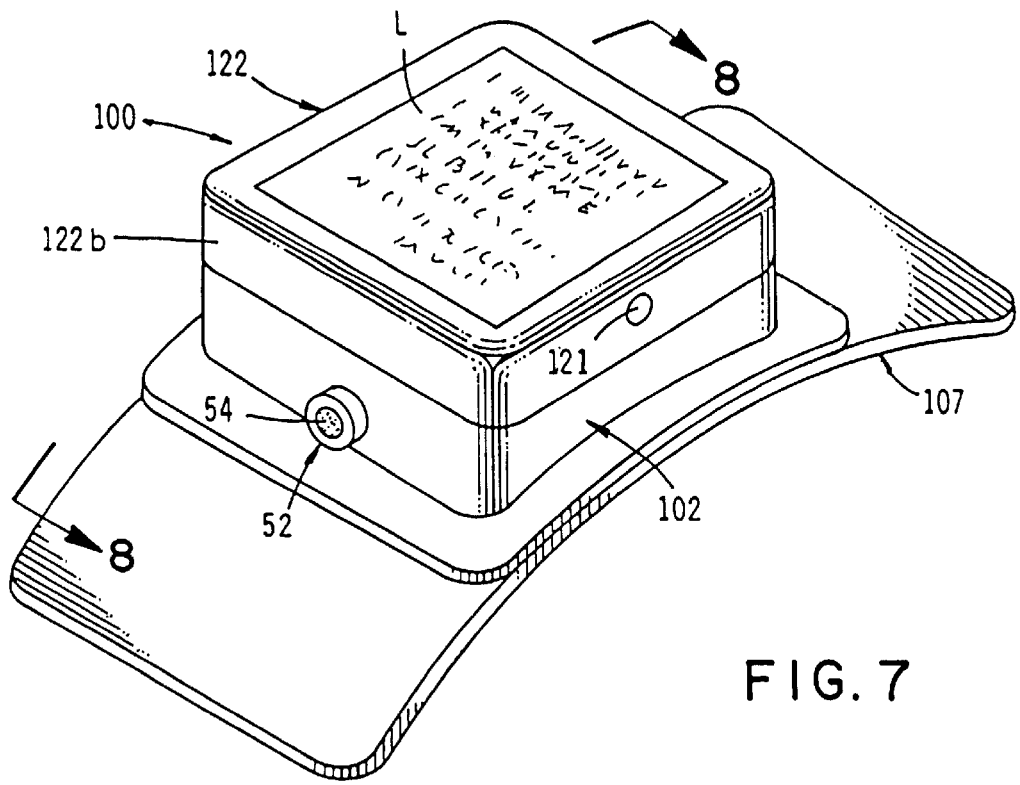
FIG. 7 is a generally perspective top view an alternate form of the ultra low profile infusion device of the invention.
Figure 8:
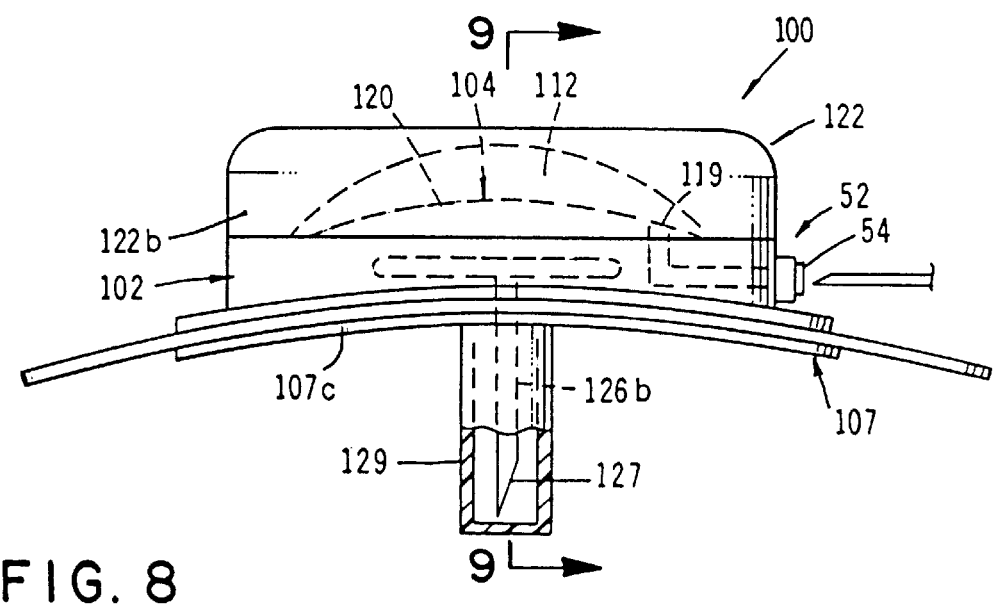
FIG. 8 is a view taken along lines 8—8 of FIG. 7.
Figure 9:
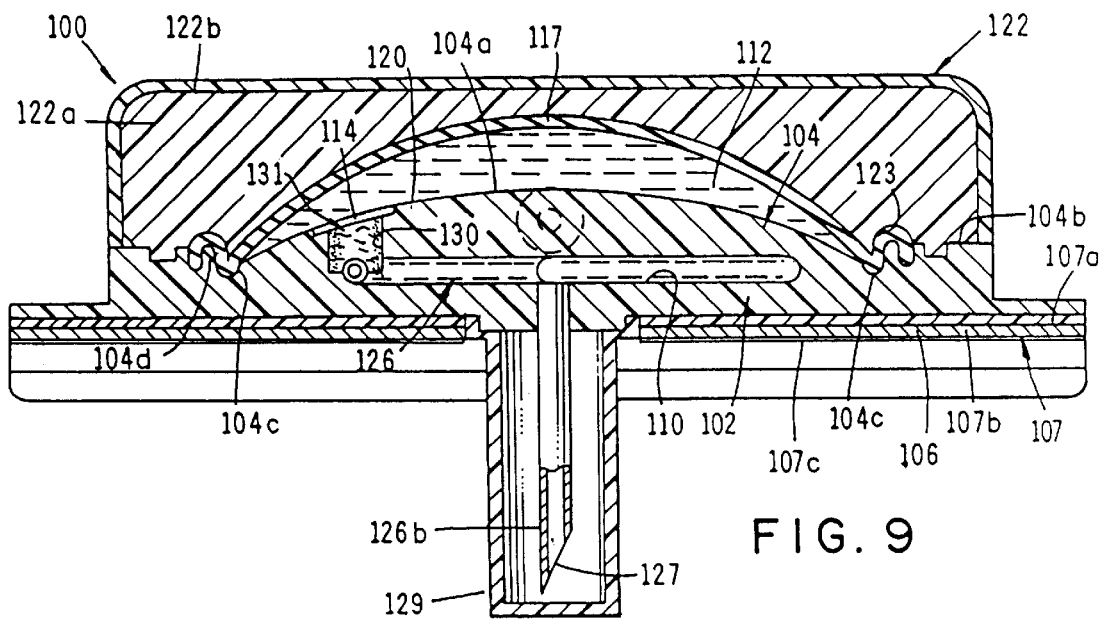
FIG. 9 is an enlarged, cross-sectional view taken along lines 9—9 of FIG. 8.
Figure 10:
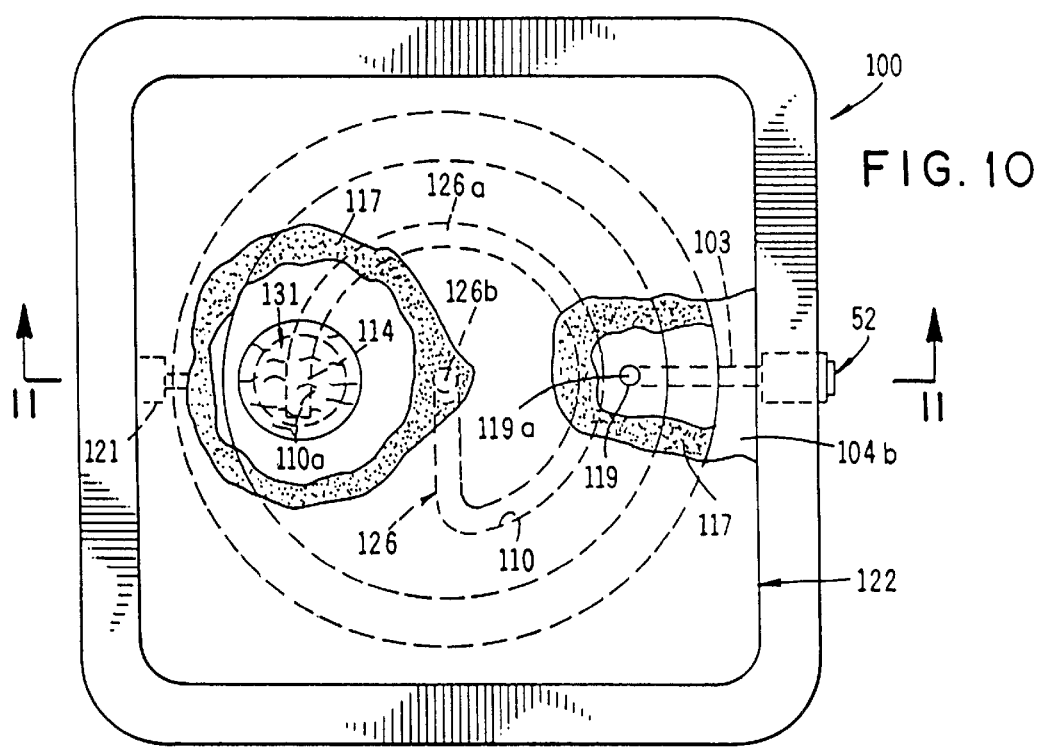
FIG. 10 is a top plan view of the device of FIG. 7 partly broken away to show internal construction.

Forming an important aspect of the apparatus of the present invention is stored energy means for forming in conjunction with base 22 a reservoir 32 having an outlet 34 (FIG. 1) which is superimposed over channel 30 in the manner shown in FIGS. 1 and 2. The stored energy means is here provided in the form of at least one distendable membrane 37 which is superimposed over base 22 and is distendable as a result of pressure imparted by fluids introduced into reservoir 32 through a fluid inlet 39 (FIG. 3). As member 37 is distended, internal stresses will be established within the membrane, which stresses tend to move the membrane toward a less distended configuration and in a direction toward base 22.

Provided within reservoir 32 is ullage defining means for engagement with membrane 37 as the membrane tends to return to its less distended configuration. The ullage defining means in the embodiment of the invention shown in FIGS. 1 through 4 comprises an upstanding, substantially rigid protuberance 40 formed on central portion 24a of base 22. Protuberance 40 is preferably integrally formed with base 22. As membrane 37 returns to toward its original configuration, it will move toward engagement with the upper surfaces of ullage protuberance 40 and in so doing will efficiently force fluid contained within reservoir 32 uniformly outwardly of the device through fluid outlet 34.

Superimposed over the base assembly, which here comprises base 22, protuberance 40 and distendable membrane 37, is a plastic cover, or enclosure 42. For certain applications, cover 42 may be constructed of a porous material and may include venting means shown here as vent "V" (FIG. 2) for venting gases, if any, contained interiorly of the cover. Additionally, medicament and instructions labels can be affixed to cover 42 to identify the medicinal fluid contained within reservoir 32 of the device.

Reference should be made to U.S. Pat. No. 5,169,389 for a discussion of the device labeling and venting and of the various materials that can be used to construct base 22, distendable membrane 37, and cover 42.

A unique aspect of the infusion device of the present invention comprises an infusion means for infusing medicinal fluid from fluid reservoir 32 into the patient. The infusion means here comprises a circuitously shaped hollow cannula 46 having a body portion 46a which is disposed within circuitous channel 30 formed in base 22 and an outlet end 46b here provided in the form of a pierceable portion which extends outwardly from base 22 for insertion into the vein of a patient. For this purpose, pierceable portion 46b includes a sharp, needle-like extremity 47 which is configured in generally the same fashion as a conventional intravenous infusion needle.

In the form of the invention shown in FIGS. 1 through 4, pierceable portion 46b of the cannula extends outwardly from base 22 in a direction generally parallel to lower surface 26 of base 22. With this unique construction, the device can be affixed to the patient's body as, for example, the arms or legs in any convenient manner, with the pierceable needle portion of the device penetrating the patient's vein. Medicinal fluid contained within reservoir 32 can then be dispensed through the cannula by means of the stored energy provided by membrane 37 which is released as the membrane tends to return toward a less distended configuration and into engagement with the ullage defining means or protuberance 40.

Forming a part of the proximal portion of the device is a protective sheath 49 for encapsulating and protecting pierceable portion 46b of the cannula. This assembly also includes web means for further assisting in securing and maintaining the penetrable portion in an appropriate invasive position to preclude intravascular trauma. Web means is here provided as a soft, flexible butterfly assemblage 49a (FIGS. 1 and 2), which is connected to base 22 and provides an appropriate surface area for taping the device to the patient.

As best seen by referring to FIGS. 3 and 4B, body portion 46a of cannula 46 is provided with a fluid inlet 46c which communicates with the outlet 34 of reservoir 32 so that fluid can flow from the reservoir into inlet 46c through cannula 46 and outwardly thereof through pierceable portion 46b.

Filling of reservoir 32 with a selected beneficial agent, or medicinal fluid, is accomplished by filling means which here comprises a septum assembly 52 which is connected to base 22 in the manner shown in FIGS. 1 and 2. Septum assembly 52 includes a pierceable septum 54 and a fill conduit 56 which communicates with cannula 46 and fluid inlet 39. As shown in FIG. 3, inlet 39, in turn, communicates with a fill orifice 58 provided in top surface 24 of base 22. With this construction, medicinal fluid can be introduced into reservoir 32 using a conventional syringe. Alternatively, the fill means can comprise a leur fitting or any other suitable fluid interconnection of a character well known to those skilled in the art by which fluid can be controllably introduced into reservoir 32 to cause distendable membrane 37 to move into its distended configuration as shown in FIGS. 3 and 4. Once again, reference should be made to U.S. Pat. No. 5,169,389 for a more complete discussion of the construction and operation of the reservoir filling means.

Forming another very important aspect of the apparatus of the present invention is fluid flow control means which is supported by base 22 at a location proximate the first end of circuitous channel 30. The fluid flow control means functions to control fluid flowing from reservoir 32 into cannula 46 and outwardly through pierceable portion 46b of the cannula. This fluid flow control means here comprises a porous member 51 which is received within a cavity 53 formed in base 22. Member 51 can be constructed of various materials such as a porous polycarbonate material available from Corning Costar Corporation and like suppliers.

Turning now to FIGS. 5 and 6, it is to be observed that the circuitously shaped cannula can be constructed in a number of different configurations including those shown in FIGS. 5 and 6. The cannula shown in FIG. 5 and generally designated as 55 has a generally Z-shaped body portion, while the cannula shown in FIG. 6 and generally designated by the numeral 57 comprises a body portion 57a which is vertically offset from the penetrable portion 57b. Depending upon the end use of the device and the configuration of base 22, cannulas having configurations such as those shown in FIGS. 5 and 6 can be appropriately positioned within corresponding circuitously shaped channels formed in base 22.

Referring next to FIGS. 7 through 14, an alternate form of the ultra low profile device of the invention is there shown and generally designated by the numeral 100. As best seen by referring to FIGS. 7, 9, and 11, the embodiment of the invention is similar in some respects to that shown in FIGS. 1 through 7. Accordingly, like numbers are used to identify like components. The apparatus here comprises a thin base 102 (FIG. 9) having an upper surface 104 including a central portion 104a and peripheral portion 104b circumscribing central portion 104a. Base 102 is provided with a lower surface 106 to which a padded assembly 107 is connected. Assembly 107 comprises a foam pad 107a to which an adhesive layer 107b is annexed. When the device is used, a very thin peal strip 107c can be stripped away so that the device can be releasably affixed to the patient. Formed within base 104 is a circuitous channel 110 (FIGS. 11 and 12), the purpose of which will presently be described.

Figure 11:
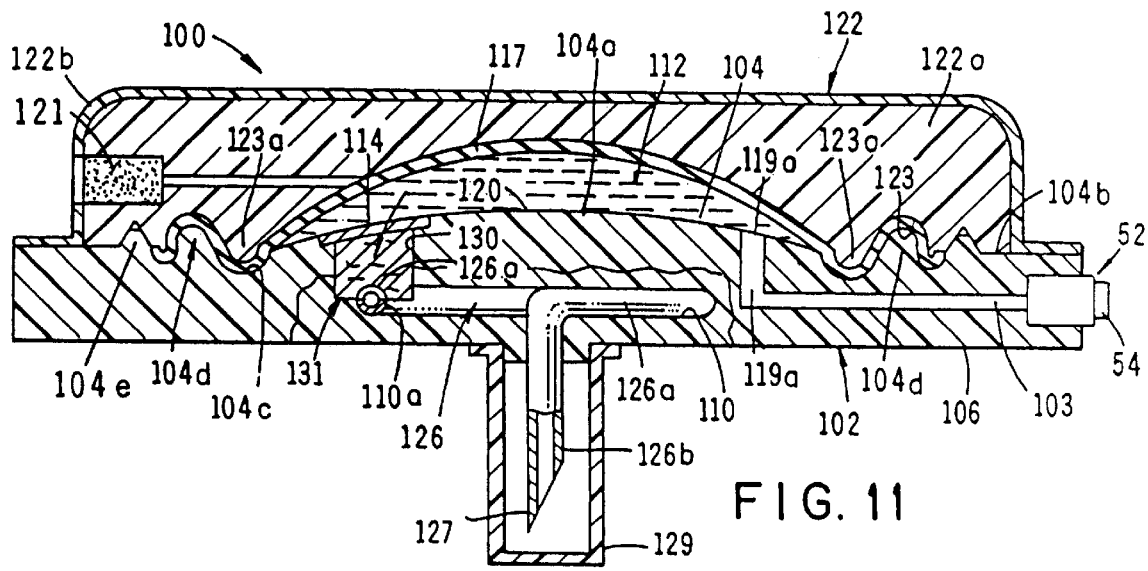
FIG. 11 is a cross-sectional view taken along lines 11—11 of FIG. 10.
Figure 12:
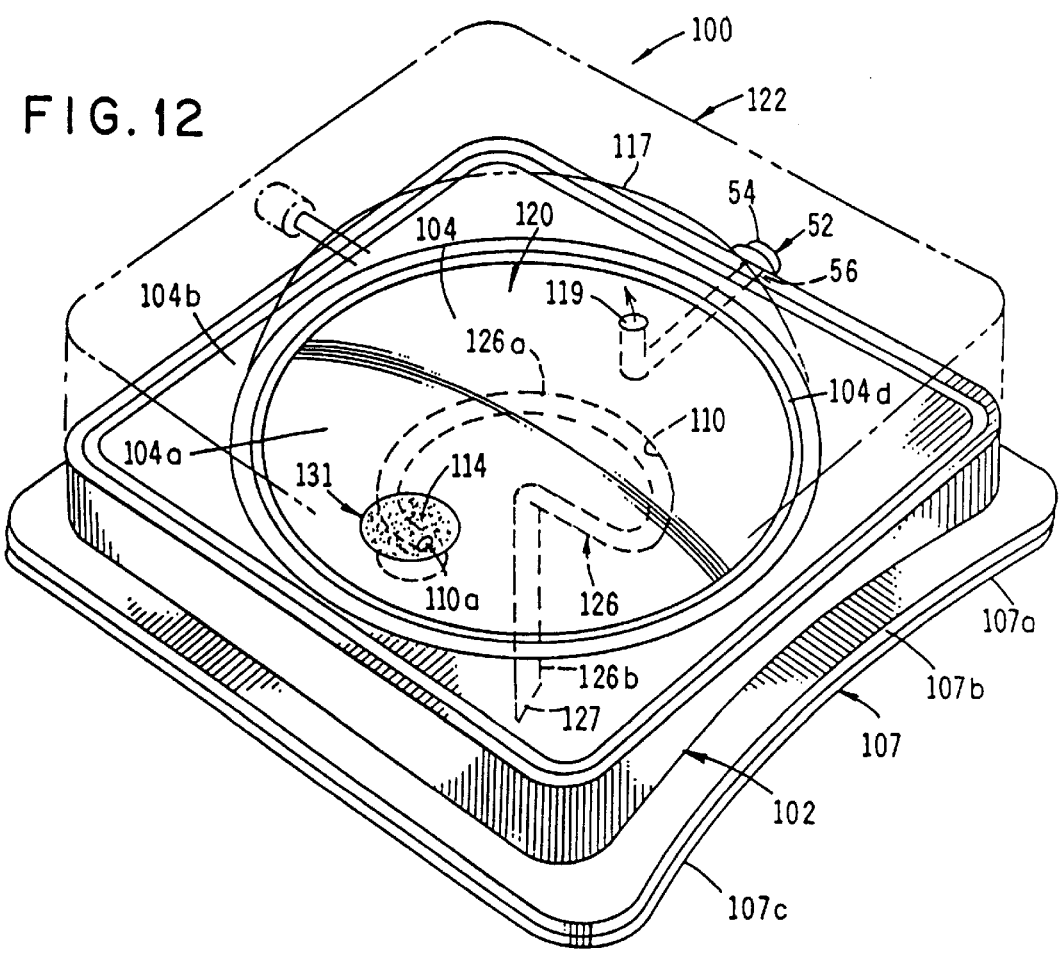
FIG. 12 is an enlarged, generally perspective view of a portion of the device shown in FIG. 7.

In the previously described embodiment, the apparatus shown in FIGS. 7 through 14 also includes stored energy means for forming in conjunction with base 102 a reservoir 112 having an outlet 114 (FIG. 12) which is superimposed over channel 110 in the manner shown in FIGS. 11 and 12. The stored energy means is here provided in the form of at least one distendable membrane 117 which is superimposed over base 102. Membrane 117 is distendable as a result of pressure imparted on the membrane by fluids introduced into reservoir 112 through a fluid inlet 119 (FIG. 11). As member 117 is distended internal stresses will be established, which stresses tend to move the membrane toward a less distended configuration and in a direction toward base 102.

Provided within reservoir 112 is ullage defining means for engagement with membrane 117 as the membrane tends to return to its less distended configuration. The ullage defining means in the embodiment of the invention shown in FIGS. 7 through 12 comprises an upstanding protuberance 120 formed on central portion 104a of base 102. As membrane 117 returns to toward its original configuration, it will move toward engagement with the upper surfaces of ullage protuberance 120 and in so doing will efficiently force fluid contained within reservoir 112 uniformly outwardly of the device through fluid outlet 114.

Superimposed over the base assembly is a plastic cover, or enclosure 122. Cover 122 includes a body portion 122a and an outer covering 122b, venting means for venting gases, if any, contained interiorly of the cover. This venting means here comprises a porous vent member 121 provided in cover 122 (FIG. 11). As before, medicament and instructions labels "L" can be affixed to cover 122 to identify the medicinal fluid contained within reservoir 112 of the device.

Once again, reference should be made to U.S. Pat. No. 5,169,389 for a discussion of the various materials that can be used to construct base 102, distendable membrane 117, and cover 122.

A unique aspect of the infusion device shown in FIGS. 7 through 14 comprises an infusion means for infusing medicinal fluid from fluid reservoir 112 into the patient. The infusion means here comprises a circuitously shaped hollow cannula 126 having a body portion 126a which is disposed within circuitous channel 110 formed in base 102 and an outlet end 126b here provided in the form of a pierceable portion extending generally perpendicularly downward from base 102 for subdermal infusion of medicinal fluids into the patient. For this purpose, pierceable portion 126a includes a sharp needle-like portion 127 which is configured in generally the same fashion as a conventional infusion needle. Unlike the earlier described embodiment of the invention, pierceable portion 126b of the cannula of the present embodiment extends outwardly from base 102 in a direction generally perpendicularly to lower surface 106 of base 102. With this unique construction, the device can be affixed to the patient's body, such as the arms or legs, in any convenient manner with the pierceable needle portion of the device penetrating the skin. Medicinal fluid contained within reservoir 112 can then be subdermally injected into the patient as membrane 117 tends to return toward a less distended configuration and into engagement with the ullage means or protuberance 120. Forming a part of the proximal portion of the device is a protective sheath 129 for encapsulating and protecting pierceable portion 126b of the cannula.

Figure 13:
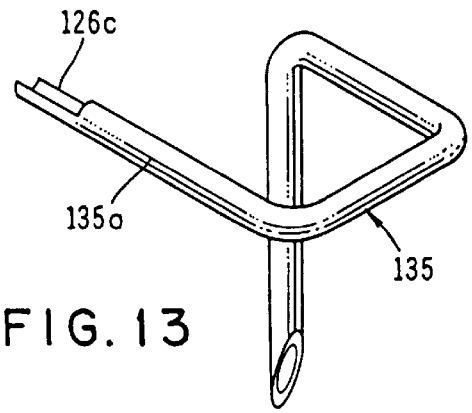
FIG. 13 is a generally perspective view of an alternate form of infusion cannula of the invention.
Figure 14:
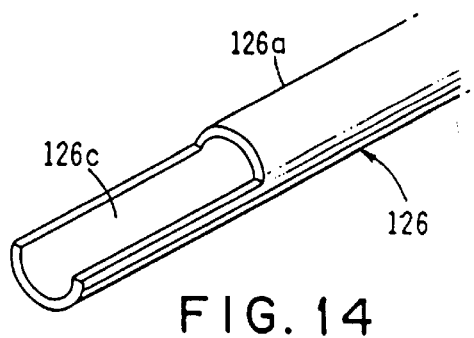
FIG. 14 is an enlarged, generally perspective view of the fluid inlet end of the infusion cannula.

As best seen in FIGS. 13 and 14, body portion 126a of cannula 126 is provided with a fluid inlet 126c which communicates with outlet 114 of reservoir 112 so that fluid can flow from the reservoir into inlet 126c and then in cannula body 126a via a fluid flow control means mounted within a cavity 130 formed in base 102.

Figure 15:
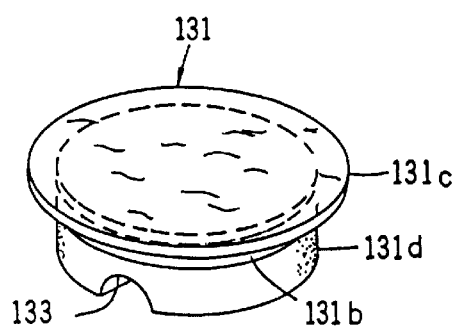
FIG. 15 is a greatly enlarged, generally perspective top view of one form of the fluid flow control assembly of the invention.
Figure 16:
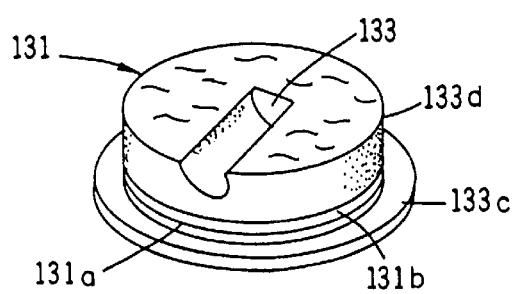
FIG. 16 is a greatly enlarged generally perspective, bottom view of the flow control assembly.
Figure 17:
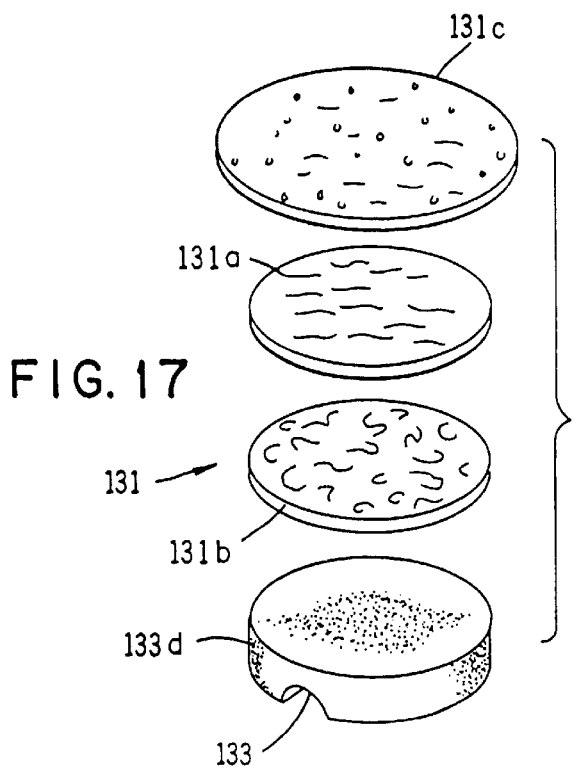
FIG. 17 is a generally perspective, exploded view of the flow control assembly of the invention of FIGS. 15 and 16.

The fluid flow control means of this latest form of the invention functions to control fluid flowing from reservoir 112 into cannula 126 and then outwardly through pierceable portion 126b of the cannula. Turning to FIGS. 15, 16, and 17, the flow control means of this latest form of the invention can be seen to comprise an assemblage of the general configuration shown in FIGS. 15 and 16 which assemblage is receivable within a cavity 130 formed in base 102 (FIG. 11). This fluid flow control assemblage, which is generally designated by the numeral 131, is of a laminate construction comprising filtering means for filtering the fluid flowing outwardly of reservoir 112 and rate control means for controlling the rate of fluid flow from reservoir 112 into cannula 126. Referring to FIG. 17, it can be seen that the filter means here comprises a filter element 131a while the rate control element comprises a disk-like rate control element 131b. Superimposed over filter element 131a is a porous disk-like seal member 131c. The assemblage comprising filter element 131a, rate control element 131b, and porous seal 131c is supported by a porous base substrate 131d having a semi-circular shaped cavity 133 which is adapted to closely receive the first end portion of cannula 126. Filter element 131a can be constructed from a wide variety materials. However, a material comprising polysulfone sold by Gelman Sciences under the name and style of SUPOR has proven satisfactory. Rate control element 131b is preferably constructed from a polycarbonate material having extremely small flow apertures ablatively drilled by an excimer laser ablation process. Both the orifice size and unit distribution can be closely controlled by this process. However, a number of other materials can be used to construct this element. Porous substrate 131d can similarly be constructed from various materials such as a porous polypropylene available from Gelman Sciences.

Turning to FIGS. 12, 13, and 14, it is to be observed that the circuitously shaped cannula can be constructed in a number of different configurations. For example, the cannula shown in FIG. 12 has a generally semi-circular shaped body portion 126a while the cannula 135 shown in FIG. 13 has a generally U-shaped body portion 135a. Both cannula construction as shown in FIGS. 12 and 13 include an inlet portion of the character shown in FIG. 14. The generally trough-shaped inlet portion 126c is disposed proximate first end 110a of channel 110 and, as shown in FIG. 11, is located directly below flow control assembly 131 so that fluid flowing through the flow control assembly will feed directly into cannula 126.

Filling of reservoir 112 with a selected beneficial agent, or medicinal fluid, is accomplished by filling means which here comprises a septum assembly 52 of the character previously described. Septum assembly 52 is connected to base 102 in the manner shown in FIGS. 10 and 11. Septum assembly 52 includes a pierceably septum 54 and a fill conduit 103 which communicates with cannula 46 and fluid inlet 119, which, in turn, communicates with fill orifice 119a provided in base 102 (FIG. 11). With this construction, medicinal fluid can be introduced into reservoir 112 using a conventional syringe.

Referring next to FIG. 12A, an apparatus for use in accomplishing the method of the invention is there illustrated. In accordance with the method of the invention for constructing the fluid delivery device, base 102 is positioned on a table "T" upon which membrane stretching means is affixed. The membrane stretching means here provided as a stretching, or elongation fixture "F", functions to bilaterally stretch the membrane in the manner shown in FIG. 12A to controllably prestress the membrane. Stretching fixture "F" comprises four circumferentially spaced membrane holding clamps 137 each having gripping elements 139 for gripping the edges of the isotropic membrane 117. Each of the clamps 137 is affixed to slide block 141 which is slidably movable along a pair of table mounted tracks 143 by means of a screw assembly 145 which is carried by an end plate 143a provided on each track 143. Each screw assembly comprises a threaded rod 145b one end of which is connected to a slide block 141. As the screw assembly is rotated by means of a handle 145a, the slide block, along with its associated clamp 137 will move outwardly relative to stationary base 102. A manual vernier 147 provided on each screw assembly provides an indication of the extent of movement of the slide block. By controlled outward movement of the slide blocks in the manner shown in FIG. 12A, the isotopic membrane will be controllably stretched and prestressed to the desired extent.

Turning to FIG. 12B, another type of apparatus usable in carrying out the method of the invention is there illustrated. This apparatus also includes a membrane stretching fixture "SF" which functions to controllably bilaterally stretch the elastomeric membrane 117 in the manner illustrated in FIG. 12B. Stretching fixture "SF" includes a plurality of circumferentially spaced hydraulically actuated membrane gripping assemblies 149, each having gripping elements for gripping the edges of the isotropic membrane. Each of the gripping assemblies 149 is mounted on a support table "T", which also supports the hydraulic equipment for operating assemblies 149. This type of equipment is of a character well known to those skilled in the art. As the gripping assemblies are actuated following a predetermined extension protocol, the gripping elements will move radially outwardly relative to the center of membrane 117 causing it to stretch either uniformly or non-uniformly depending on the end use of the device. It is to be understood that for certain end use applications of the apparatus, the stored energy membrane need not be prestressed.

Also forming a part of the apparatus of FIG. 12A is a centrally disposed sonic welding apparatus "SW", which can be used in a manner well known by those skilled in the art to interconnect cover assembly 122 to base 102. Surrounding the sonic welder are vacuum operated article pick-up devices "PU", which can be used to position the cover assembly of the fluid delivery device relative to the membrane during the assembly operation. Each of these pick-up devices includes a generally circular shaped gripping member 151 which is rotatable about a support shaft 151a.

After the membrane has been appropriately prestressed, the next step in the method of the invention comprises affixing the prestressed membrane to the peripheral portion 104b of the upper surface of base 102. This is accomplished by moving cover assembly 122 downwardly relative to base 102 in a manner such that prestressed membrane 117 will be securely clamped between the peripheral portions of cover 122 and the peripheral portion of the base (see FIGS. 9 and 11). As the cover is moved toward base 102, the central portion of membrane 117 will engage and conform to the ullage defining means or protuberance 104.

Cover 122 as well as membrane 117 can be interconnected with the base as by sealably bonding them to the base 102 in various ways well known to those skilled in the art, such as, for example, adhesive or sonic bonding. In the embodiment of the invention shown in FIGS. 9 and 11, peripheral portion 104b of base 102 is provided with a capture groove 104c and an adjacent tongue 104d. Body portion 122a of assembly cover 122, on the other hand, is provided with a groove 123 and a tongue 123a (FIG. 11) which mate with groove 104c and tongue 104d respectively as the cover moves into engagement with base 102. Base 102 is further provided with an upstanding membrane cutting means or protuberance 104e (FIG. 11) which functions to cleanly cut membrane 117 upon cover 122 being brought into pressural engagement with base 102. With this construction, following cutting of the membrane the cover can be sonically welded to the base in the proximity of the upstanding tongue of the base and the mating groove in the cover by techniques well understood by those skilled in the art. After the sonic welding step, the cover and membrane are securely interconnected with the base in a manner to provide a sealed enclosure for the distendable membrane.

Figure 20:
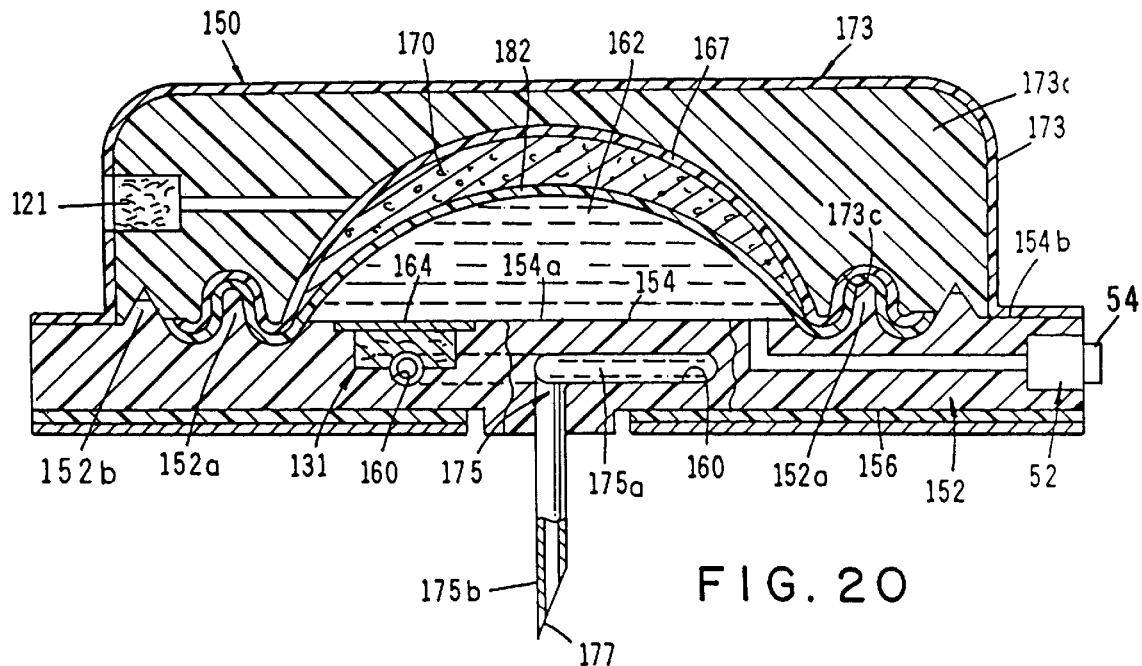
FIG. 20 is a cross-sectional view of yet another embodiment of the invention showing an infusion device embodying a novel conformable ullage rather than rigid ullage.

Referring to FIGS. 20 and 21, still another form of the ultra low profile device of the invention is there shown and generally designated by the numeral 150. As best seen by referring to FIG. 20, this latest embodiment of the invention is similar in some respects to that shown in FIGS. 7 through 12. Accordingly, like numbers are used to identify like components. The apparatus here comprises a base 152 having an upper surface 154, including a central portion 154a and peripheral portion 154b circumscribing central portion 154a. Base 152 is also provided with a lower surface 156. Formed within base 152 is a circuitous channel 160, which receives the infusion means of the invention.

As in the previously described embodiments, the apparatus shown in FIGS. 20 and 21 also includes stored energy means for forming in conjunction with base 152 a reservoir 162 having an outlet 164. Outlet 164 is superimposed over channel 160 in the manner shown in FIG. 20. Filling of reservoir 162 is accomplished in the same manner as previously described herein in connection with the embodiment shown in FIGS. 7 through 12 using septum assembly 52.

The stored energy means is here provided in the form of at least one distendable membrane 167 which is superimposed over base 152. As before, an ullage defining means is disposed within reservoir for engagement with membrane 167 which, after being distended, will tend to return to its less distended configuration. The ullage defining means of this latest embodiment of the invention is of a totally different and highly novel character from that previously described. More particularly, the ullage defining means here comprises a conformable ullage which uniquely conforms to the shape of the distendable membrane, as the membrane tends to return to its less distended configuration in the manner shown in FIG. 20A. The conformable ullage, which is identified in FIGS. 20 and 20A by the numeral 170, can be constructed as a deformable mass from a number of materials such as various types of gels, foams, fluids and soft elastomers. In some instances the conformable ullage may comprise an integral conforming mass. In other instances, such as when a gel or fluid is used as the ullage medium, an encapsulation barrier membrane is used to encapsulate the ullage medium.

A highly novel aspect of the conformable ullage of the invention resides in the fact that it can be located either between the base and the fluid to be delivered or, alternatively, as shown in FIG. 20, can be located between the distendable membrane and the fluid to be delivered. Additionally, as will be discussed in the paragraphs which follow, a plurality of subreservoirs can be associated with a single ullage thereby making it possible to provide a wide variety of different medicament delivery regimens.

Because the ullage defining means can be located in various locations within the reservoir, the central portion of the base is, as shown in FIG. 21, substantially flat. This type of base can, of course, be used with an ullage configuration of the character shown in FIG. 20 and can also be used with a variety of different ullage configurations, the details of which will presently be described.

Figure 18:
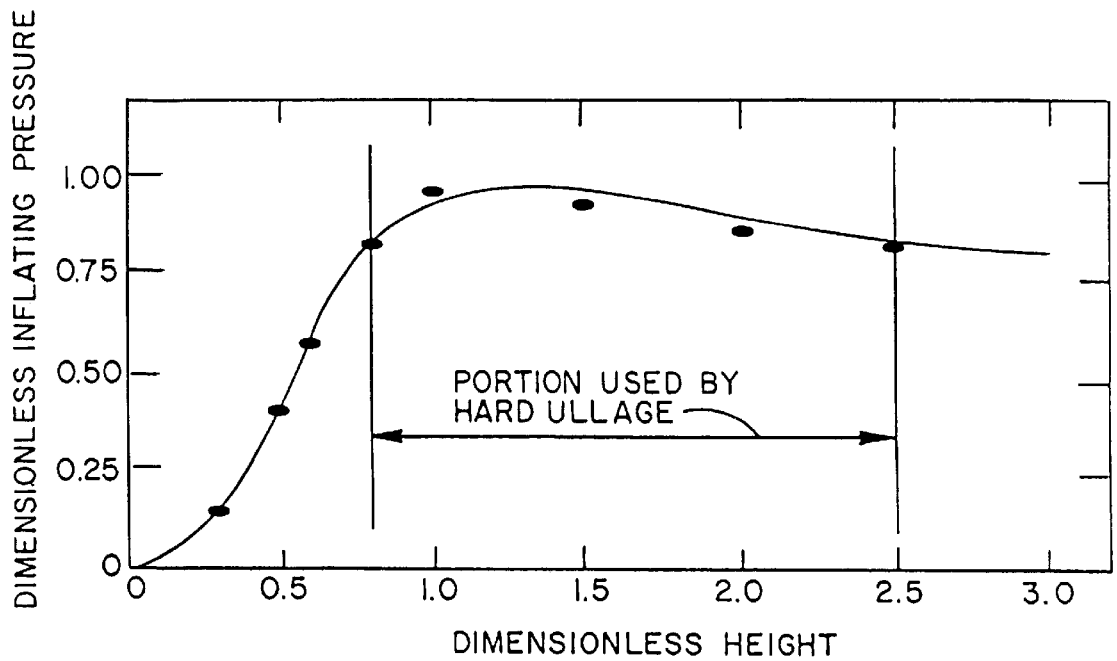
FIG. 18 is a graphical representation of the range of extension of the distendable membrane in a rigid ullage type of construction.

Before discussing the number of conformable ullage configurations that are possible in constructing the fluid delivery devices of the invention, a brief discussion will be undertaken of the several operational advantages that are inherent in the conformable ullage construction. For example, the rigid ullage construction, such as is shown in FIGS. 1 through 14, requires that the stored energy elastomeric membrane be used at high extensions over a significantly large pressure curve. This condition is illustrated in FIG. 18 wherein inflating pressure is plotted against height. Further, the elastomeric membrane materials that are suitable for use as the stored energy means must possess certain specific physical characteristics in order to meet the performance requirements for the fluid delivery apparatus. For example, depending on the end use of the device, the elastomeric membrane material must have good memory characteristics under conditions of high extension, good resistance to chemical and radiological degradation and appropriate gas permeation characteristics.

Once an elastomeric membrane material is chosen that will optimally meet the desired performance requirements of the fluid delivery device, there are still limitations to the level of refinement of the delivery tolerances that can be achieved using the rigid ullage configuration. These refinements are due primarily to the inability of the rigid ullage to satisfactorily conform to the shape of the elastomeric membrane near the end of the fluid delivery cycle. This nonconformity can lead to extended delivery rate tail off and higher residual problems that are undesirable when extremely accurate delivery is required. For example, when larger volumes of fluid are to be delivered, the tail-off volume represents a smaller portion of the fluid amount delivered and, therefore, exhibits much less effect on the total fluid delivery profile. However, in very small dosages, the tail-off volume becomes a larger portion of the total volume. This places physical limits on the range of delivery profiles that can acceptably be accommodated by the rigid ullage configuration.

The elastomeric membrane material candidates for use in the rigid ullage construction must also be drug compatible since the membrane will typically be in contact with the drug containing fluid that is introduced into the reservoir. Many currently available elastomeric membrane materials, due to their chemical composition or means of manufacturing, are not suitably drug compatible. This compatibility restriction, combined with strict physical requirements and material properties characteristics, results in further limitation of available selections for the candidate elastomeric material for use in the rigid ullage design.

The apparatus of the invention illustrated in FIG. 20 provides a unique and novel improvement over the rigid ullage type devices and, as will become apparent from the discussion which follows, can be adapted to many end use applications. More particularly, this novel embodiment of the invention includes the previously identified conformable ullage 170 that can be constructed of various materials that will elegantly satisfy the tighter delivery tolerance requirements of the device, while at the same time effectively overcome the limitations of materials selection encountered in devices embodying the rigid ullage configuration.

Figure 19:
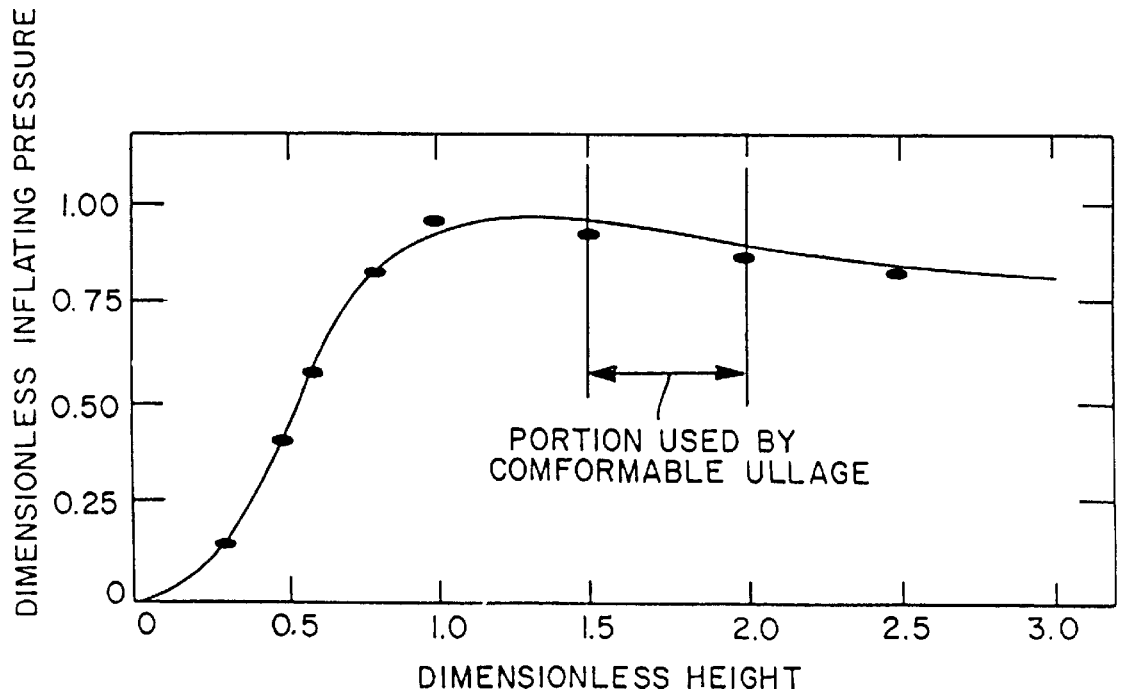
FIG. 19 is a graphical representation of the range of extension of the distendable membrane in a conformable ullage type of construction.

As previously mentioned, the unique characteristics of the conformable ullage of this latest form of the invention permits the ullage to be placed either above or below the fluid reservoir in relation to the base. For example, when, as indicated in FIG. 19, the conformable ullage is positioned above the medicament reservoir, a much smaller portion of the pressure-deformation curve can be used, thus enabling the stored energy membrane to undergo less deformation during the fluid delivery process. Less deformation of the stored energy membrane, in turn, minimizes the changes in the linearity of the resulting fluid delivery profile. Further, because the small portion of the pressure-deformation curve that is used can be taken from a lower elongation level (FIG. 19), the viscoelastic effect is reduced. The viscoelastic effect reduces the level of stored energy in the membrane over time, which translates into lower rates of energy membrane stress relaxation over time. This is a most important performance design factor for devices requiring prolonged shelf life having extended delivery profiles.

Referring once again to FIG. 20, in the construction of the device there shown, a cover assembly 173 is superimposed over base 152. Cover assembly 173 includes a body portion 173a, an outer covering 173b, and venting means comprising a porous vent member 121 of the character previously described. This latest form of the invention also includes an infusion means for infusing medicinal fluids from fluid reservoir 162 in the patient. The infusion means comprises a circuitously shaped hollow cannula 175 of the character previously described having a body portion 175a which is disposed within circuitous channel 160 formed in base 152 and an outlet end 175b here provided in the form of a pierceable portion extending generally perpendicularly downward from base 152 for subdermal infusion of medicinal fluids into the patient. For this purpose, pierceable portion 175b includes a sharp, needle-like portion 177. Forming a part of the proximal portion of the device is a protective sheath 179 for encapsulating and protecting pierceable portion 175b of the cannula (FIG. 21).

During the step of filling reservoir 162, which is accomplished in the manner previously described, the fluid being introduced into the reservoir under pressure via septum assembly 52 will cause a pusher member 182, which is affixed proximate its periphery to base 152, to engage conformable ullage 170 urging it outwardly against distendable membrane 167. As the membrane is thus distended, internal stresses will be formed in the membrane tending to return it to the less distended configuration shown in FIG. 20A. As this occurs membrane 167 will exert forces on conformable ullage 170 which will controllably move it toward base 152. However, when ullage 170 engages base 152, in the manner shown in FIG. 20A, it will uniquely conform to the upper surface of the base as well as the three dimensional shape of distendable membrane 167. In this way, the conformable ullage will permit the distendable membrane to provide a constant fluid expelling pressure on the fluid contained within the reservoir throughout the fluid delivery cycle, thereby avoiding undesirable delivery rate tail off at the end of the delivery period. This novel linear performance permits the device to meet even the most stringent medicinal fluid delivery requirements.

During the fluid delivery step described in the preceding paragraph, fluid will flow from reservoir 162, through outlet 164, through a flow control means and into the inlet through 175c of cannula 175 (FIG. 21a). The flow control means here comprises a flow control assembly 131 of the character shown in FIGS. 15, 16, and 17 and as previously described herein.

Figure 20A:
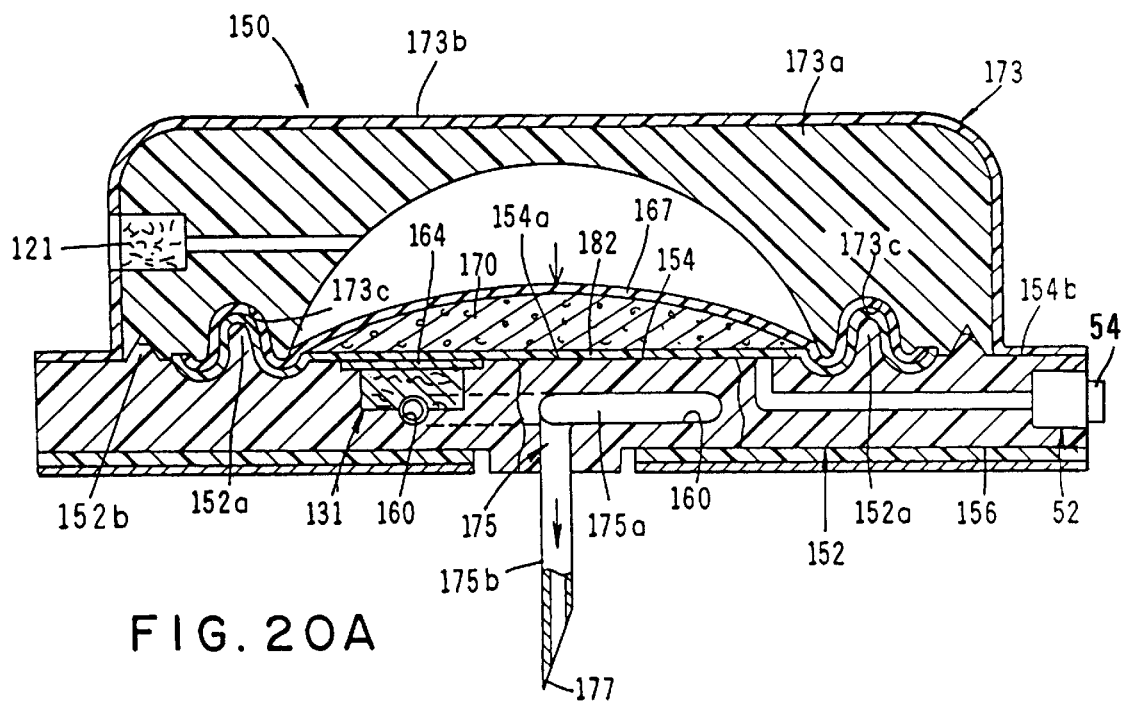
FIG. 20A is a cross-sectional view similar to FIG. 20, but showing the configuration of the device after the fluid has been dispensed therefrom.

Distendable membrane along with pusher member 182 are secured to base 152 in the manner shown in FIG. 20A. More particularly, the peripheral portion 154b of base 152 is provided with a tongue 152a which mates with a groove 173c provided in cover assembly 173 as the cover assembly moves into engagement with base 152. Base 152 is also provided with an upstanding, circumferentially extending membrane cutting means or protuberance 152b (FIG. 11) which functions to cleanly cut membrane 167 and pusher 182 upon cover assembly 173 being brought into pressural engagement with base 152. Protuberance 152b also functions as a sonic energy director for the sonic weldment of base 152 and cover 173. With this construction, following cutting of the membrane and the pusher member, the cover can be sonically welded to the base in the proximity of the upstanding tongue of the base and the mating groove in the cover by techniques well understood by those skilled in the art. After the sonic welding step, the cover, membrane, and pusher member are all securely interconnected with the base in a manner to provide a sealed enclosure.

Turning to FIG. 22, still a further form of the ultra low profile device of the invention is there illustrated and generally designated by the numeral 200. This embodiment of the invention is similar in some respects to that shown in FIGS. 20 and 21 and, therefore, like numbers are used in FIG. 22 to identify like components. This apparatus is unique in that it includes two separate fluid containing reservoirs and a conformable ullage disposed between the reservoirs and the stored energy means. As before, the apparatus comprises a thin base 202 having an upper surface 204 including a generally planar central portion 204a and a peripheral portion 204b circumscribing the central portion. Formed within base 202 is a circuitous channel 206 that receives a circuitously shaped cannula 208.

The apparatus shown in FIG. 22 also includes stored energy means for forming in conjunction with base 202 first and second reservoirs 210 and 212. Reservoir 212 has an outlet 214 while reservoir 210 has an outlet 216 both of which are superimposed over a circuitous channel 206. Both reservoirs communicate with cannula 208 via flow control means here shown as first and second flow control assemblies 218 and 220. The stored energy means is here provided in the form of at least one distendable membrane 224 which is superimposed over base 202 and is affixed therewith in the manner shown in FIG. 22 and as described in connection with the earlier discussed embodiments.

As was the case with the embodiment of the invention shown in FIGS. 20 and 21, pierceable portion 208b of the cannula extends outwardly from base 202 in a direction generally perpendicularly to lower surface of the base. With this construction, medicinal fluids contained within reservoirs 210 and 212 can then be subdermally injected into the patient as membrane 224 tends to return toward the less distended configuration shown in FIG. 22C and into engagement with the ullage means or a conformable ullage 225 which is of similar construction to conformable ullage 170. As shown in FIG. 22E, this arrangement of reservoirs results in a two phase flow rate delivery profile. Initially, the injection flow rate results from the medicinal fluid flowing from both reservoirs 210 (R1) and 212 (R2). In the latter portion of the flow delivery profile, and after the fluid in reservoir 212 is expanded, only the remaining medicinal fluid in reservoir 210 contributes to the flow. The greater flow rate in the first phase is intended to accommodate periods where a higher dosage rate is required, such as the basal delivery rate for insulin during the daytime. The second phase with its lower flow rate is then suitable for the basal rate delivery of insulin during the night when less is required. In this manner, one delivery apparatus may be used for an entire 24 hour period.

As indicated in FIG. 22D, body portion 208a of cannula 208 is provided with a first fluid inlet 226 which communicates with outlet 216 of reservoir 210 so that fluid can flow from this reservoir into the flow control assembly 218 and then in cannula 208. In similar fashion, reservoir 212 communicates with a second fluid inlet 228 provided in cannula 208 via outlet 214 and flow control assembly 220. Flow control assemblies 218 and 220 are of identical construction to the assemblage shown in FIGS. 15, 16, and 17 and operate in the same manner to control fluid flow from the two reservoirs outwardly into cannula 208 shown in FIG. 22. A cover assembly 225 covers base 202 in the manner shown in FIG. 22.

During the filling step, reservoir 212 is first filled by fluid introduced into a passageway 228 (FIG. 22) via a first septum assembly 51 which is provided in base 202 in a spaced apart relationship with a second septum assembly 52. Fluid under pressure flowing through passageway 228 will engage a pusher membrane 230 which is affixed at its peripheral upper surface 204 of base 202. Following filling of reservoir 212, reservoir 210 is next filled using the second septum assembly 52 which is in fluid communication with a passageway 229 formed in base 202. As fluid under pressure enters reservoir 210 via passageway 229, conformable ullage 225 will be urged outwardly against distendable membrane 224 causing the membrane to move outwardly against the inner surface 225a of cover assembly 225. As the membrane is thus distended, internal stresses will be formed within the membrane.

Upon opening the outlet or delivery port of the device, the distended membrane 224 will exert forces on conformable ullage 225 which will controllably move it toward base 202 in the manner shown in FIG. 22C. As before, during the infusion step, the ullage will uniquely conform to the three dimensional shape of the distendable membrane and fluid contained within reservoir 210 and 212 will be controllably expelled from the device. During the infusion step the, distendable membrane functions to provide a constant, uniform pressure on the fluid within the two reservoirs thereby avoiding any undesirable delivery rate tail off near the end of the delivery period.

Figure 23:
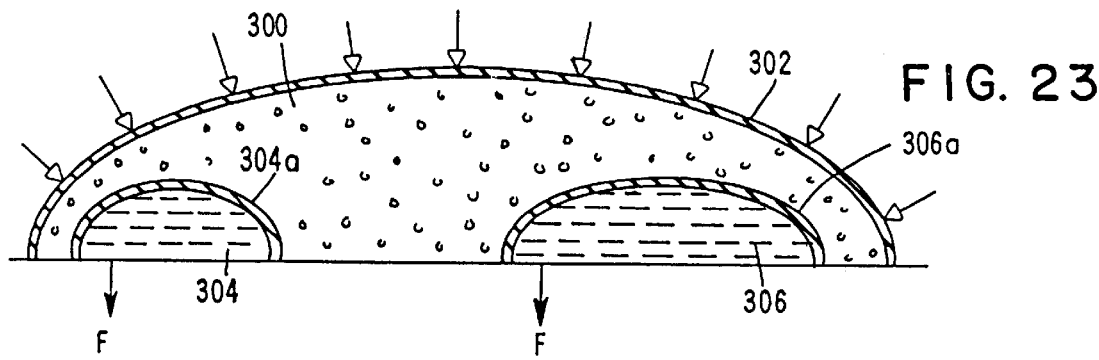
FIG. 23 is a generally diagrammatic view of yet another form of conformable ullage construction of the invention showing two fluid filled subreservoirs.
Figure 24:
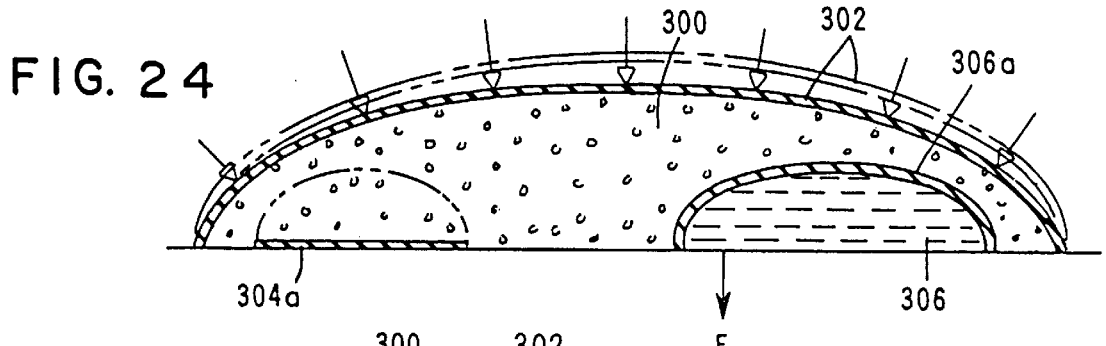
FIG. 24 is a generally diagrammatic view similar to FIG. 23, but showing one of the subreservoirs having been emptied of fluid.
Figure 25:
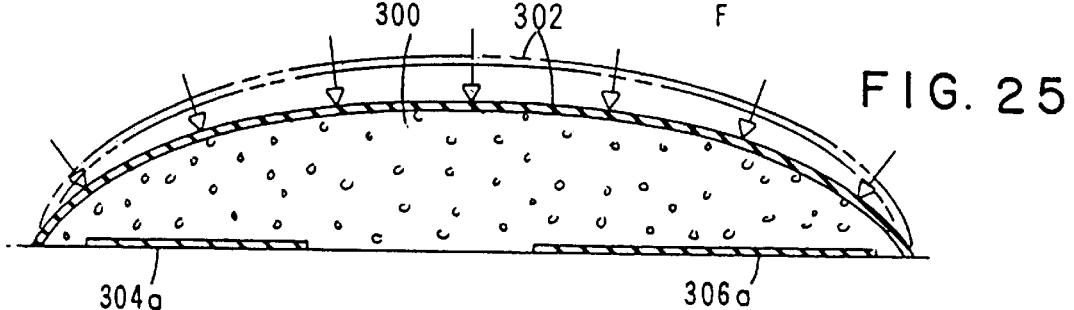
FIG. 25 is a generally diagrammatic view similar to FIG. 24 but, showing both of the subreservoirs having been emptied.

Turning next to FIGS. 23, 24, and 25, yet another conformable ullage, distendable membrane and reservoir only construction is there diagrammatically illustrated. In this instance the conformable ullage 300 is disposed between distendable membrane 302 and first and second spaced apart fluid reservoirs 304 and 306 each having separate fluid inlets and fluid outlets. With this construction the contents of the reservoirs can be delivered sequentially by first opening the outlet of reservoir 304 and then by opening the outlet of reservoir 306. Once again, the stored energy source, or elastomeric membrane 302 will act upon the conformable ullage which, in turn, will act upon the reservoirs to cause the fluid contained therein to be controllably expelled through the delivery port of the device. For example, as shown in FIG. 24, when the outlet of reservoir 304 is opened, ullage 300 will be urged downwardly against a yieldable pusher member 304a which defines the extent of reservoir 304, causing fluid to be expelled from the reservoir. Similarly, when the outlet of reservoir 306 is opened, ullage 300 will be urged downwardly against a deformable pusher member 306a which, along with the base define the extent of reservoir 306, causing the fluid contained within the reservoir to be controllably expelled (FIG. 25, the arrows "F" indicating outward fluid flow via flow control means).

Figure 26:
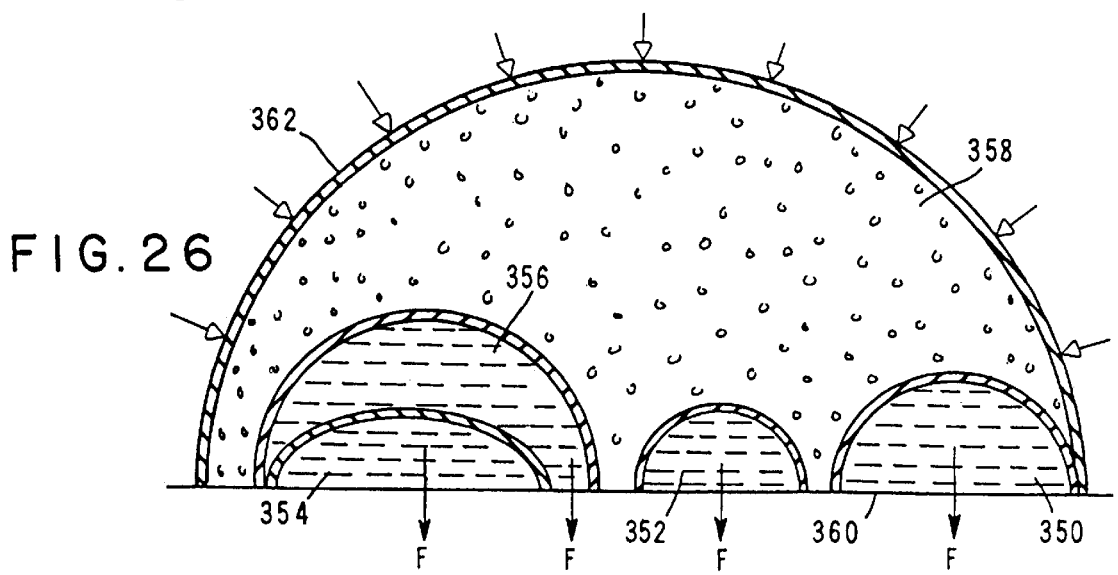
FIG. 26 is a generally diagrammatic view of still another form of conformable ullage construction of the invention showing four subreservoirs.

Further exemplifying the remarkable versatility of the conformable ullage construction of the present invention is the arrangement diagrammatically illustrated in FIG. 26, wherein four separate reservoirs 350, 352, 354, and 356 are acted upon by the conformable ullage 358 as it is urged toward base 360 by the stored energy means or distendable membrane 362. As indicated in FIG. 26, reservoirs 350, 352, and 354 are transversely spaced along the upper surface of the base of the device, while reservoir 356 is superimposed over reservoir 354. Each of these reservoirs is provided with a separate inlet so that different fluids can be introduced into each reservoir. In like manner, each reservoir is provided with its own outlet so that the fluids contained within the reservoir can be sequentially dispensed as the distendable membrane acts upon the conformable ullage 358 in the manner previously described.

It is to be understood that in the case of the constructions diagrammatically illustrated in FIGS. 22 through 26, the pressure exerted on the fluid reservoirs of the device can be varied depending upon the distendable membrane material properties, material thickness, footprints and the extension of the membrane. Altering the conformable ullage configuration along with the variations in the number and placement of fluid reservoirs which are to be acted upon by the ullage makes it possible to readily match a very large number of drug delivery protocols.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

We claim:

1. A fluid delivery device comprising:
   (a) a thin base having an upper surface including a central portion and a peripheral portion circumscribing said central portion, a lower surface and a channel formed in said base intermediate said upper and lower surfaces said channel having first and second ends;
   (b) a stored energy means for forming in conjunction with said base, a reservoir having an outlet, said stored energy means comprising at least one distendable membrane superimposed over said base, said membrane being distendable as a result of pressure imparted by fluids introduced into said reservoir to establish internal stresses, said stressed tending to move said membrane toward a less distended configuration;
   (c) ullage defining means carried by said base for engagement by said distendable membrane as said membrane moves toward a less distended configuration;
   (d) means for delivering fluid from said fluid reservoir, said means having an inlet end disposed proximate said first end of said channel and further including:
      (i) a body portion disposed within said channel formed in said base; and
      (ii) an outlet end provided in the form of a portion extending outwardly from said second end of said channel and in a direction substantially perpendicular to said lower surface of said base.

2. A device as defined in claim 1 in which said ullage-defining means comprises a protuberance formed on said central portion of said base and extending into said reservoir.

3. A device as defined in claim 1 further including fluid inlet means for introducing fluid into said fluid reservoir, said fluid inlet means comprising a pierceable septum connected to said base.

4. A device as defined in claim 1 further including flow control means in communication with said reservoir and carried by said base for delivering fluid from said fluid reservoir in a controlled manner.

5. A fluid delivery device comprising:
   (a) a thin base having an upper surface including a central portion and a peripheral portion circumscribing said central portion, a lower surface and a channel formed in said base intermediate said upper and lower surfaces said channel having first and second ends;
   (b) a stored energy means for forming in conjunction with said base, a reservoir having an outlet, said stored energy means comprising at least one distendable membrane superimposed over said base, said membrane being distendable as a result of pressure imparted by fluids introduced into said reservoir to establish internal stresses, said stresses tending to move said membrane toward a less distended configuration;
   (c) ullage defining means carried by said base for engagement by said distendable membrane as said membrane moves toward a less distended configuration, said ullage defining means comprising a yieldable mass that is substantially conformable to the shape of the distendable membrane as said membrane tends to move toward a less distended configuration;
   (d) means for delivering fluid from said fluid reservoir, said means having an inlet end disposed proximate said first end of said channel and further including:
      (i) a body portion disposed within said channel formed in said base; and
      (iii) an outlet end provided in the form of a portion extending outwardly from said second end of said channel.

6. A fluid delivery device comprising:
   (a) a thin base having an upper surface including a central portion and a peripheral portion circumscribing said central portion, a lower surface and a channel formed in said base intermediate said upper and lower surfaces said channel having first and second ends;
   (b) stored energy means for forming in conjunction with said base, a reservoir having an outlet, said stored energy means comprising at least one distendable membrane superimposed over said base, said membrane being distendable as a result of pressure imparted by fluids introduced into said reservoir to establish internal stresses, said stressed tending to move said membrane toward a less distended configuration;

(c) ullage defining means carried by said base for engagement by said distendable membrane as said membrane moves toward a less distended configuration;

(d) means for delivering fluid from said fluid reservoir, said means having an inlet end disposed proximate said first end of said channel and further including:
  (i) a body portion disposed within said channel formed in said base; and
  (ii) an outlet end provided in the form of a portion extending outwardly from said second end of said channel; and (e) flow control means in communication with said reservoir and carried by said base for delivering fluid from said fluid reservoir in a controlled manner, said flow control means comprising a filter element for filtering the fluid flowing from said reservoir and a rate control element for controlling the rate of fluid flow outwardly of said portion of said means for delivering fluid from said reservoir.

7. A device as defined in claim 6 in which said flow control means further includes a porous substrate for supporting said filter element.

8. A device for use in infusing medicinal fluid into a patient at a controlled rate comprising:

(a) a base having an upper surface including a central portion, and a peripheral portion circumscribing said central portion and a lower surface;

(b) stored energy means for forming in conjunction with said base, a reservoir having an outlet, said stored energy means comprising at least one distendable membrane superimposed over said base, said membrane being distendable as a result of pressure imparted by fluids introduced into said reservoir to establish internal stresses, said stresses tending to move said membrane toward a less distended configuration; and (c) ullage-defining means carried by said base for engagement by said distendable membrane, said ullage-defining means comprising a mass substantially conformable to the shape of said distendable membrane as said membrane tends to move toward a less distended configuration.

9. A device as defined in claim 8 in which said mass comprises a gel.

10. A device as defined in claim 8 in which said mass comprises a fluid.

11. A device as defined in claim 8 in which said mass comprises an elastomer.

12. A device as defined in claim 8 in which said reservoir contains a medicinal fluid and in which said mass is disposed between said base and said fluid.

13. A device as defined in claim 8 in which said reservoir contains a medicinal fluid and in which said mass is disposed between said distendable membrane and said medicinal fluid.

14. A device as defined in claim 8 in which said base further includes a circuitous channel having first and second ends formed between said upper and lower surfaces, a cannula having an inlet end disposed proximate said first end of said circuitous channel and in communication with said outlet of said reservoir, said cannula further includes an outlet end provided in the form of a pierceable portion extending outwardly from said second end of said circuitous channel for insertion into the patient.

15. A device as defined in claim 14 in which said pierceable portion extends outwardly in a direction substantially perpendicular to said lower surface of said base for subdermal infusion of fluid into the patient.

16. A device as defined in claim 14 further including flow control means for controlling fluid flow through said cannula, said flow control means being disposed within a cavity formed in said base at a location between said fluid outlet of said reservoir and said inlet end of said cannula.

17. A device as defined in claim 16 in which said flow control means comprises a filter element for filtering the fluid flowing from said reservoir and a rate control element for controlling the rate of fluid flow outwardly of said pierceable portion of said cannula.

18. A device as defined in claim 17 in which said flow control means further includes a porous substrate for supporting said filter element and said rate control element, said porous substrate having a channel for receiving said inlet end of said cannula.

19. A fluid delivery device comprising:

(a) a base;

(b) stored energy means for forming, in conjunction with said base, a reservoir having an outlet, said stored energy storage means comprising at least one distendable member superimposed over said base, said member being distendable as a result of pressure imparted by fluids introduced into said reservoir to establish internal stresses, said stresses tending to move said member toward a less distended configuration;

(c) a conformable ullage disposed proximate said distendable member, said conformable ullage being substantially conformable with said distendable member as said member moves toward said less distended configuration; and (d) an outlet port for dispensing fluids from the device.

20. A device as defined in claim 19 in which said conformable ullage comprises a gel.

21. A device as defined in claim 19 in which said conformable ullage comprises a fluid.

22. A device as defined in claim 19 in which said conformable ullage comprises a cellular mass.

23. A device as defined in claim 19 in which said reservoir contains a medicinal fluid and in which said conformable ullage is disposed intermediate said distendable membrane and said medicinal fluid.

24. A device as defined in claim 19 in which said reservoir includes a plurality of subreservoirs each said sub-reservoir containing a different medicinal agent.

25. A device as defined in claim 24 in which said sub-reservoir are separated by a yieldable reservoir membrane.

26. A device as defined in claim 24 in which a selected one of said sub-reservoirs is separated from said conformable ullage by a yieldable membrane.

27. A device for use in infusing medicinal fluid into a patient at a controlled rate comprising:

(a) a base having an upper surface and a lower surface engageable with the patient and a circuitous channel formed in said base intermediate said upper and lower surfaces, said circuitous channel having first and second ends and an intermediate portion disposed therebetween;

(b) stored energy means for forming in conjunction with said base, a reservoir having an outlet, said stored energy means comprising at least one distendable membrane superimposed over said base, said membrane being distendable as a result of pressure imparted by fluids introduced into said reservoir to establish internal stresses, said stresses tending to move said membrane toward a less distended configuration; and (c) infusion means for infusing medicinal fluid from said fluid reservoir into the patient, said infusion means comprising a circuitously shaped hollow cannula having:

(i) an inlet end portion disposed proximate said first end of said circuitous channel;

(ii) a non-linear central body portion disposed within said intermediate portion of said circuitous channel; and (iii) an end portion having a first segment disposed proximate said second end of said channel and a second segment comprising a pierceable portion extending outwardly from said second end of said channel for insertion into the patient.

28. A device as defined in claim 27 in which said pierceable portion of said hollow cannula extends angularly outwardly from said non-liner central body portion of said hollow cannula.

29. A device as defined in claim 28 in which said pierceable portion of said hollow cannula extends substantially perpendicularly from said lower surface of said base.

30. A method of making a low profile device for use in infusing medicinal fluid into a patient at a controlled rate having a base provided with an upper surface including a central portion and a peripheral portion circumscribing the central portion, a distendable, elastomeric membrane superimposed over the base, and a cover engageable with the base to enclose the distendable membrane therewithin, the method comprising the steps of:

(a) gripping the distendable membrane in a manner to differentially stretch the membrane to produce a prestressed membrane;

(b) subsequent to stretching the membrane, placing said prestressed membrane over the upper surface of the base;

(c) emplacing the cover over the base and the prestressed membrane; and (d) sealably interconnecting the prestressed membrane with the peripheral portion of the base.

31. A method as defined in claim 30 including the steps of sealably bonding the prestressed membrane to the peripheral portion of the base.

32. A method as defined in claim 30 including the further step of cutting the prestressed membrane as the cover is emplaced over the base.

33. A method as defined in claim 32 including following the step of cutting the prestressed membrane, sealably bonding the cover to the peripheral portion of the base.

34. A method of making a fluid delivery device for use in infusing medicinal fluid into a patient having a base provided with an upper surface including a central portion and an upstanding tongue circumscribing the central portion, a distendable elastomeric membrane superimposed over the base, and a cover engagable with the base to enclose the distendable membrane therewithin, the cover having a groove within which the tongue of the base is closely receivable, the method comprising the steps of:

(a) stretching the distendable membrane to produce a prestressed membrane;

(b) urging the prestressed membrane into engagement with the upper surface of the base and into engagement with the upstanding tongue of the base;

(c) emplacing the cover over the base and the prestressed membrane such that the membrane is clamped between the tongue of the base and the groove of the cover;

(d) cutting the prestressed membrane at a location proximate the upstanding tongue of the base to provide a cut, prestressed membrane;

(e) sealably interconnecting the cut, prestressed membrane and the cover with the peripheral portion of the upper surface of the base.

35. A method as defined in claim 34 in which the cover is bonded to the base by sonic welding of the cover to the base at a location proximate the upstanding tongue of the base.

36. A method of making a device for use in infusing medicinal fluid into a patient at a controlled rate having a base provided with an upper surface including a central portion and a peripheral portion circumscribing the central portion, a distendable, elastomeric membrane superimposed over the base, the method comprising the steps of:

(a) producing a prestressed membrane from a starting elastomeric membrane by the step of exerting forces on said starting elastomeric membrane in a manner to produce internal stesses therewithin to form a prestressed membrane;

(b) following the step of forming the prestressed membrane, placing the prestressed membrane over the base; and (c) interconnecting the prestressed membrane with the base.

* * * * *